(12) United States Patent
Boumsellek et al.

(10) Patent No.: US 8,173,959 B1
(45) Date of Patent: May 8, 2012

(54) REAL-TIME TRACE DETECTION BY HIGH FIELD AND LOW FIELD ION MOBILITY AND MASS SPECTROMETRY

(75) Inventors: Saïd Boumsellek, San Diego, CA (US); Thomas J. Kuehn, Potomac Falls, VA (US)

(73) Assignee: Implant Sciences Corporation, Wilmington, MA (US)

( * ) Notice: Subject to any disclaimer, the term of this patent is extended or adjusted under 35 U.S.C. 154(b) by 855 days.

(21) Appl. No.: 11/941,939

(22) Filed: Nov. 17, 2007

Related U.S. Application Data

(60) Provisional application No. 60/951,205, filed on Jul. 21, 2007.

(51) Int. Cl.
*H01J 49/26* (2006.01)
(52) U.S. Cl. ........ 250/288; 250/281; 250/282; 250/290; 250/291
(58) Field of Classification Search .......... 250/281, 250/282, 283, 288, 290, 291, 292, 293, 295, 250/296, 297
See application file for complete search history.

(56) References Cited

U.S. PATENT DOCUMENTS

| | | | |
|---|---|---|---|
| 6,495,823 B1 | 12/2002 | Miller et al. | |
| 6,809,313 B1 * | 10/2004 | Gresham et al. | 250/287 |
| 7,057,168 B2 | 6/2006 | Miller et al. | |
| 2003/0038235 A1 * | 2/2003 | Guevremont et al. | 250/287 |
| 2004/0149902 A1 * | 8/2004 | Park | 250/288 |
| 2005/0051719 A1 * | 3/2005 | Miller et al. | 250/287 |
| 2005/0109930 A1 * | 5/2005 | Hill et al. | 250/286 |
| 2006/0219889 A1 * | 10/2006 | Shvartsburg et al. | 250/282 |
| 2008/0073502 A1 * | 3/2008 | Schneider et al. | 250/282 |
| 2008/0142700 A1 * | 6/2008 | Dahl et al. | 250/286 |
| 2008/0179515 A1 * | 7/2008 | Sperline | 250/290 |
| 2008/0237458 A1 * | 10/2008 | Wang | 250/282 |

FOREIGN PATENT DOCUMENTS

| | | |
|---|---|---|
| WO | 0008454 A1 | 2/2000 |
| WO | 0008455 A1 | 2/2000 |
| WO | 0008456 A1 | 2/2000 |
| WO | 0008457 A1 | 2/2000 |
| WO | 2007014303 A2 | 2/2007 |

OTHER PUBLICATIONS

Buryakov, I.A, et al., "Separation of ions according to mobility in a strong ac electric field," Sov. Tech. Phys. Lett., 17(6), Jun. 1991, pp. 446-447 (translation). Buryakov, I.A, et al., "A new method of separation of multi-atomic ions by mobility at atmospheric pressure using a high-frequency amplitude-asymmetric strong electric field," International Journal of Mass Spectrometry and Ion Processes, 128, 1993, pp. 143-148.

* cited by examiner

*Primary Examiner* — David A Vanore
*Assistant Examiner* — Nicole Ippolito
(74) *Attorney, Agent, or Firm* — Jerry Turner Sewell

(57) ABSTRACT

A trace detection system includes at least two stages coupled to operate in series. An ion mobility spectrometer (IMS) stage has a sampling inlet to receive a sample to be analyzed. An ion source ionizes the sample. The IMS applies an electrical field to the ionized sample to move the ionized sample toward an IMS outlet. A differential mobility spectrometer (DMS) stage coupled in series with the IMS stage receives the ionized sample from the IMS stage. Preferably, the system includes a mass spectrometer (MS) stage coupled in series with the DMS stage to receive the ionized sample from the DMS stage via a vacuum interface. A roughing vacuum pump evacuates a first stage of the MS stage to a first pressure below atmospheric pressure. A high vacuum pump evacuates a second stage of the MS stage to a second pressure below the first pressure.

17 Claims, 22 Drawing Sheets

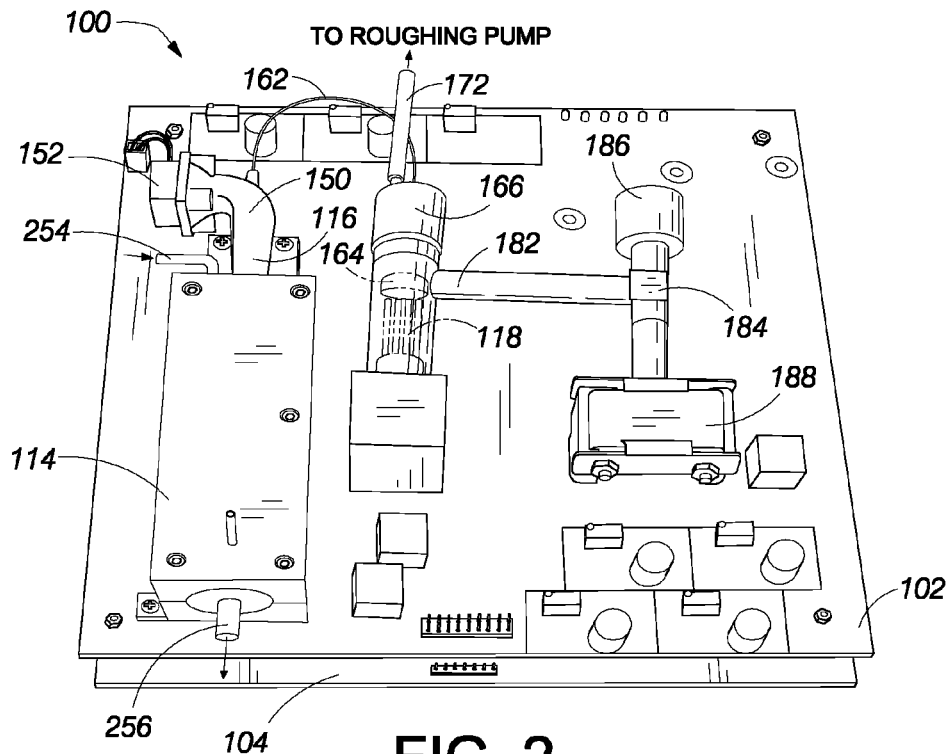
FIG. 2
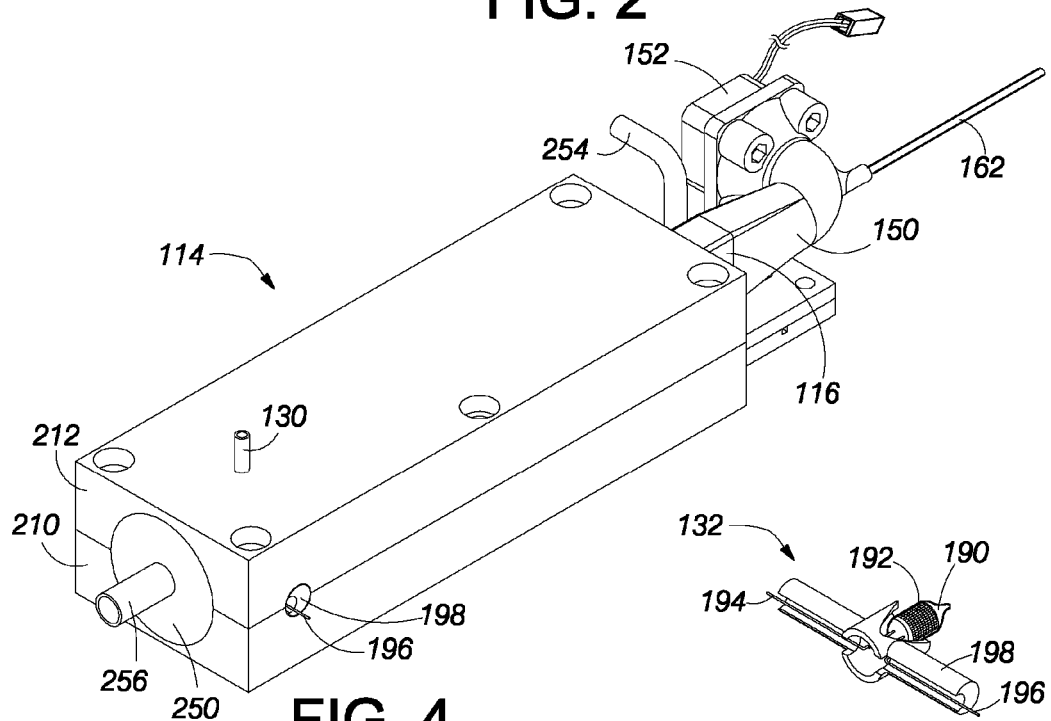
FIG. 4
FIG. 3 ic field and an ion mobility analyzer that filters the ionized molecules according to the mobilities of the ionized molecules in an electric field.

REAL-TIME TRACE DETECTION BY HIGH FIELD AND LOW FIELD ION MOBILITY AND MASS SPECTROMETRY

RELATED APPLICATIONS

The present application claims the benefit of priority under 35 USC §119(e) to U.S. Provisional Application No. 60/951,205, filed on Jul. 21, 2007.

BACKGROUND OF THE INVENTION

1. Field of the Invention

The present invention relates to portable systems and methods for real-time detection, identification and analysis of trace amounts of chemical materials for such applications as environmental, health and safety monitoring, product quality testing and control, and detection of narcotics, contraband, explosives and chemical and biological agents.

2. Description of the Related Art

Trace detectors are commonly used to detect small amounts of materials, such as, for example, toxic chemicals, product contaminants, counterfeit drugs, narcotics, explosives, chemical and biological materials. Conventional trace detectors rely on collecting and extracting small representative samples of the chemical or biological material of interest ("target analyte") from air, gas, water, soils, surfaces or other environmental matrices in which the target analytes are usually found. For example, conventional trace explosives detectors rely on the availability of sufficient samples of the explosive compound, chemical precursors or binders, and/or taggants in the form of a vapor or particulate residues on the skin, clothing, baggage and personnel items of people that have come in direct or indirect contact with the explosive. Such reliance is based on the assumption that since many explosive particles have a high sticking coefficient, it is difficult to avoid contamination by the particles when the banned materials are handled, such as during the process of making a bomb or other explosives device. However, the same high sticking coefficient results in extremely low vapor pressures for the particles, which causes detection of the particles to be challenging.

Vapor samples, particle samples or both are acquired for some conventional trace explosives detectors by swiping "suspect" surfaces of luggage, personal items or persons with a swab or the like and placing the swab in the detector. In other conventional systems using portals, pulses of compressed air are directed at the person in the portal to liberate particles off the person's clothing, skin, shoes, etc., and to transport the liberated particles to the detector.

In both types of conventional trace explosives detectors mentioned above as well as other trace detection systems, the sample is introduced into an Ion Mobility Spectrometer (IMS) for analysis. The sample includes analyte molecules (molecules to be analyzed for a potential explosive threat or other target analyte) and background molecules. In the IMS, the analyte molecules and the background molecules are typically ionized using radioactive alpha emitters or beta emitters, and the ions are injected into a drift tube with a constant low electric field (200 volts/centimeter or less) where the molecules are separated on the basis of their respective drift velocities and hence their respective mobilities. The mobilities of the ions are governed by the ion collisions with the drift gas molecules flowing in the opposite direction. The ion-molecule collision cross section of an ion depends on the size, the shape, the charge, and the mass of the ion relative to the mass of the drift gas molecule. The resulting chromatogram is compared to a library of known patterns to identify the substances collected. Since the collision cross section depends on more than one ion characteristic, peak identification is not unique. An IMS system measures a secondary and less specific property of the target molecule—the time it takes for the ionized molecule to drift through a tube filled with a viscous gas under an electric field—and the identity of the molecule is inferred from the intensity versus time spectrum produced by the IMS system. Since different molecules may have similar drift times, an IMS system inherently has less chemical specificity than a mass spectrometer (MS).

IMS-based trace detectors are simple, low cost, and operate at atmospheric pressure; however, IMS-based trace detectors exhibit major shortcomings that make them unsuitable for addressing a variety of emerging threats or other target analytes of interest for various applications. Such limitations include, for example, (1) high false alarm rates due to limited resolution (chemical specificity), which makes IMS vulnerable to interfering molecules, (2) exacerbation of the high false alarm rates near the detection threshold, (3) decreased probability of detection (false negatives) due to higher alarm thresholds, (4) limited and fixed (predetermined) range of detectable explosives threats or other target analytes, and (5) a need to frequently calibrate the detectors by running standards in the presence of various backgrounds.

Recently, alternative technologies have been considered that have requirements that emphasize the reduction of costly false alarm rates, that increase instrument throughput, that implement non-intrusive automated sample collection, and that increase the probability of detection. Mass spectrometers (MS) are strongly considered for use as trace detectors. Because of its powerful analytical capability, a mass spectrometer avoids most of the problems associated with IMS. For example, mass spectrometers are used in a wide range of applications that include environmental monitoring, pharmaceutical drug discovery, and petrochemical processing industries. For trace detection technology, MS-based systems offer some advantages over currently deployed IMS systems. The advantages include lower alarm threshold (by at least a factor of 100) while maintaining low false alarm rates by greater chemical specificity (a factor of 1000 better using medium resolution MS). The uniqueness of mass spectrometry lies in the chemical specificity as the mass spectrometer directly measures a fundamental property of the target molecule—its molecular weight—and thus provides a highly specific means of identifying the molecule. MS-based systems also enable a broader range of target analytes to be concurrently detectable including a broader range of explosives such as peroxide and liquid explosives, chemical warfare agents, and some warfare biological agents. However, progress in the widespread deployment of MS-based detection instruments has been stalled for the past two decades. In particular, mass spectrometers are bulky (e.g., greater than 100 pounds) and costly (e.g., greater than $50,000). Mass spectrometers are also complex instruments that require highly trained personnel to operate the instruments and to interpret the data produced by the instruments. Mass spectrometers require high vacuum to operate, which requires cumbersome vacuum pumps to reduce the atmospheric pressure to a pressure below 1 milliTorr.

SUMMARY OF THE INVENTION

Aspects of embodiments in accordance with the present invention include a mass analyzer that filters ionized molecules according to the mass-to-charge ratios of the molecules by subjecting the molecules to an electric or magnetic field. Mass analyzers include time-of-flight, magnetic sector, quadrupole, hyperbolic ion trap, ion cyclotron resonance, and several variations of these basic designs.

Time-of-flight (TOF) instruments are similar to IMS in that they are non-scanning devices. In particular, ions of different masses are accelerated to a given energy and are separated based on their flight time between the ionization region and a fast-response detector inside a drift tube in vacuum. The TOF method is the fastest (several microseconds) type of mass analysis and is ideal for pulsed ionization sources. The TOF method is also ideal for coupling with IMS devices since the time domains of the two instruments are very different. In fact TOF instruments are able to perform IMS peak profiling by recording several mass spectra within a single IMS peak.

Quadrupole instruments are scanning devices in which ions of different masses are sequentially filtered. Quadrupole instruments require a continuous source of ions. Quadrupole mass filters remain the design of choice in numerous applications because of to their simplicity and robustness. Since quadrupole mass filters are scanning devices, quadrupole mass filters are able to perform targeted analysis by searching for compounds from a list rather than scanning continuously an entire mass spectrum hence reducing the scan time. Conventional quadrupole mass filters comprise four poles arranged in a matrix-like pattern on which a combination of a radio frequency (RF) electric field and a DC electric field is applied. The same polarity is applied to diagonally opposed poles. Within the mass filter constituted by the space between the poles, ions experience oscillations at different frequencies and hence are dispersed. By varying the amplitude of the RF field, ions with different mass-to-charge ratio are stabilized within the filter and successfully reach the detector. The DC field component determines the resolving power of the mass filtering process.

The chemical selectivity of the systems disclosed herein is further enhanced by coupling MS with gas chromatography (GC) or liquid chromatography to create a tandem GC-MS instrument or by coupling MS with IMS to create a tandem IMS-MS instrument. Such tandem instruments are referred to herein as hyphenated instruments. In the GC-MS instruments, the GC separates analyte molecules from background gasses in complex mixtures such as air prior to injecting the analyte molecules into the MS for analysis. In the IMS-MS instruments, the IMS separates analyte ions from the background gasses prior to injecting the analyte ions into the MS for analysis. Such hyphenated techniques make it possible to eliminate undesired background gasses and to distinguish between ions with the same mass-to-charge ratio.

While GC-MS instruments are powerful laboratory analytical instruments, the use of GC-MS instruments as high throughput field instruments is limited. In addition to size, weight, and complexity constraints, limitations of such instruments include elution times of several minutes through the GC columns and long refreshing times between samples. On the other hand, IMS chromatograms are obtained in a fraction of a second. Combining IMS and MS overcomes the selectivity limitations of IMS-only systems and the speed limitations of GC-MS instruments. With a lower limit of detection, the MS instrument provides deterministic detection and identification of traces of compounds. Increased sensitivity, selectivity and speed qualify an IMS-MS instrument as a strong alternative for field trace detection. At such high analysis speeds, the screening cycle time and therefore the throughput are governed by the sample collection and preparation time rather than the analysis time. Furthermore, MS-based systems provide wider and automatically reconfigurable ranges of detectable chemical analytes including explosives, chemical and biological warfare agents.

The use of IMS instruments as front-end filters accomplishes two major goals. (1) Target analytes are pre-separated. (2) With the drift gas flowing in the opposite direction of the ion flow, the MS is not exposed to background gasses and hence is kept "clean." However, since the mobility value of IMS instruments is independent of the applied electric field, ions with the same or similar mobility may not be readily separated. Compared to IMS, DMS (differential mobility spectrometry) or high-field asymmetric-waveform ion mobility spectrometry (FAIMS) instruments use a high-frequency asymmetric RF waveform applied between two parallel electrodes or metal plates. This waveform alternates between a short, high-field (approximately 15,000 volts/centimeter) pulse and an opposite polarity, longer, low-field pulse. At the higher electric field, the mobilities of all ions become dependent on the electric field. As a result, even ions with the same low-field ion mobilities may often be separated. Since the ions experience different mobilities during the high and low electric field segments of the waveform, the ions drift towards one plate or the other depending on their charge. The ion dispersion is stopped by applying a small DC voltage or compensation voltage (CV) to either of the plates. By scanning the CV over a range of voltages, a differential mobility spectrum is generated. The DMS apparatus may be set to pass one specific ion continuously (constant CV), making it an ideal continuous source of ions in front of a quadrupole mass spectrometer, which dramatically reduces the background observed. This ensures that only the target analyte ions are injected into the vacuum for mass analysis. The earliest DMS analyzers employed parallel planar electrodes to separate ions produced by atmospheric gas-phase ionization methods.

In accordance with the embodiments disclosed herein, a trace detector comprises a miniature mass spectrometer (MS) that is combined with an IMS followed by a DMS as front-end filters to produce a hyphenated (i.e., tandem) IMS-DMS-MS. In addition to increased selectivity, hyphenating (i.e., combining in tandem) conventional ion mobility, differential ion mobility, and mass spectrometry provides an increased signal-to-noise ratio since increasing the number of separation stages decreases the chemical noise at a faster rate than the signal. Extensive miniaturization fits all three instruments into a portable trace detector that can be operated in nearly real-time for immediate detection of threat analytes. Furthermore, since the MS operates in vacuum, novel miniature pumps are included in one embodiment of the detector system. An advantage of miniaturized versions of full-size instruments is increased ruggedness, making the instruments suitable for field use. The challenge with miniaturization is recovering the signal loss since shrinking the dimensions of the separation stages reduces the acceptance areas and therefore the signals by the square of the shrinkage factor. However, ion losses through the multiple analysis stages and through the vacuum interface (in the case of the IMS-DMS-MS) are significantly reduced by using appropriately shaped ion funnels based on the geometry of the ion sampling areas.

The hyphenated IMS-DMS-MS concept is based on the integration and the convergence of ground breaking innovations in: (1) miniature mass spectrometry (MS); (2) miniaturization and MEMS (micromachined electromechanical systems) fabrication of IMS and DMS devices; (3) miniature vacuum pumping; (4) low cost, low power non radioactive soft ionization source, and (5) efficient collection of surface particle and vapor samples. The innovative IMS-DMS and IMS-DMS-MS system and method disclosed here provide up to three separate orthogonal detection methods (mobility, charge, and/or mass) in a single trace explosives detector that uniquely achieves extremely low false alarm rates with high sensitivity, selectivity, and specificity of detection and deterministic identification of target explosives.

The three analytical devices can be operated in different modes, which results in overall flexibility by adapting the hyphenated instrument to the application's requirements. For example, such a technique provides a new generation of detectors to meet the goal for rapid, on-site screening of explosives inside and outside vehicles, on individuals and on carry-on objects at checkpoints, and interrogation of suspect objects and persons in large gatherings such as political conventions and sports events. In the IMS-DMS-MS system and method disclosed herein, all background signals are eliminated so that it is not necessary to run standards in the presence of all known backgrounds, as is always necessary with IMS. The IMS-DMS-MS system has hardware level flexibility so that the instruments can be reconfigured and optimized to exploit different trade-offs suitable for a variety of detection scenarios for different lists of target compounds.

The IMS-DMS-MS design concept may employ any suitable type of mass spectrometer depending on the specific application. In the exemplary embodiment, the IMS-DMS-MS system is anchored by an advanced version of the Ion Metrics, Inc. quadrupole array mass sensor (QAMS), its associated microelectronics, and miniature vacuum pumps. The QAMS is the core enabling technology that meets the requirements for on-site, portable and low cost miniature sensor for fast and unambiguous detection to confirm the presence of target analytes, such as explosives, chemical warfare agents, narcotics, and toxic industrial chemicals. The QAMS has unparalleled advantages making it extremely suitable for on-site and portable applications. The QAMS is a miniature 4×4 array of 1-millimeter diameter poles that provide nine parallel quadrupoles. Using an inexpensive manufacturing process based on glass-to-metal seal technology, the 16 poles are aligned and are secured in a glass chassis, which also serves as the vacuum seal. The length of the mass filter is advantageously between 20 millimeters and 30 millimeters, which enables the filter to operate linearly at pressures as high as 1 milliTorr. The sensor is generally cylindrical and has a height of approximately 1.5 inch and a diameter of approximately 0.5 inch, which reduces the dimensions of the vacuum chamber to a few cubic centimeters. The small size of the mass filter and the ability of the mass filter to operate at high pressures reduce the vacuum pumping requirements and therefore reduce the overall size and weight of the instrument since vacuum pumps account for a significant percentage of the size and weight of the instrument. The sensors are driven by equally miniaturized high frequency RF (7 MHz) high voltage (1000 volts peak-to-peak) power supplies, which enable operation over a mass range up to 500 atomic mass units (amu) with a mass resolution of 0.5 amu measured at full width half maximum (FWHM).

The small size, low power, and low cost of the IMS-DMS-QAMS system cause the system to be particularly suitable for field use. The system is readily deployable at multiple checkpoints, is easily incorporated into sensor networks, and can be embodied in a portable detector across the full range of security inspection and screening applications. Multiple sensors at checkpoints and in the hands of security agents provide high throughput inspections and wide coverage of improvised explosives devices (IED) threats in public transportation and security venues. In high volume applications such as surveillance, IMS-DMS-QAMS system units can be deployed with arrays of ionizers capable of handling larger air volumes and can be mounted at strategic locations to monitor areas of high human traffic, such as, for example, in subways and in lobbies of government, military and financial buildings.

In mass spectrometry, the detection approach utilizes one of the most powerful analytical techniques in terms of accuracy, sensitivity, selectivity, and speed for the detection and identification of explosives and other chemical compounds. Compared to ion mobility, which is the technique of choice of conventional explosives detection, mass spectrometry does not rely on the presence of nitro groups or metallic elements for detection. For example TATP, an IED used by many groups because of its ease of synthesis, and other peroxide explosives molecules represent a challenge since they do not include nitro groups. The high specificity and resolution provided by the QAMS analyzer allows the identification of other more volatile chemical pre-cursors, binders, stabilizers and taggants that may be present on or near the IEDs in addition to the signatures of explosives compounds themselves. This capability facilitates detection of explosives and volatile signatures in the proximity of the device by direct air sampling and sample enrichment through micro-machined thermal desorbers in addition to non-contact surface interrogation of suspect vehicles, packages, or persons.

While the disclosed solution to trace detection is primarily based on a mass spectrometry (MS) approach in order to minimize false alarms, miniature ion mobility spectrometers are used as front-end filters to enhance the device's selectivity. In order to efficiently sample complex mixtures such as air, miniature two-gate IMS and parallel plates DMS spectrometers are incorporated into the system as pre-screeners. Such filters reduce the interferences which cause false alarms. Having the IMS in front of the DMS, the counter flow of the IMS keeps the DMS and the QAMS clean as significantly fewer neutrals are transferred downstream. Using the outlet gate of the IMS, only ions of interest are injected into the DMS. In addition to improving the DMS peak widths, injecting only ions of interest contributes to reducing ion molecule reactions in the DMS, which complicate the DMS spectrum when real samples are analyzed. The tandem IMS-DMS approach and the tandem IMS-DMS-QAMS approaches offer additional flexibility in optimizing the trade-offs between selectivity and sensitivity. The flexibility of analysis is based on over determination by performing up to three orthogonal measurements including mass spectra, compensation voltage spectra, and drift time.

BRIEF DESCRIPTION OF THE DRAWINGS

Certain aspects in accordance with embodiments of the present invention are described below in connection with the accompanying drawing figures in which:

FIG. 2 illustrates a perspective view of an embodiment of the system of FIG. 1 looking from the top;

FIG. 3 illustrates a perspective view of an exemplary distributed plasma ion source (DPIS) used in the embodiment of FIGS. 1 and 2;

FIG. 4 illustrates a perspective view of an exemplary ion mobility spectrometer (IMS) used in the embodiments of FIGS. 1 and 2;

DETAILED DESCRIPTION OF THE PREFERRED EMBODIMENTS

Figure 1:
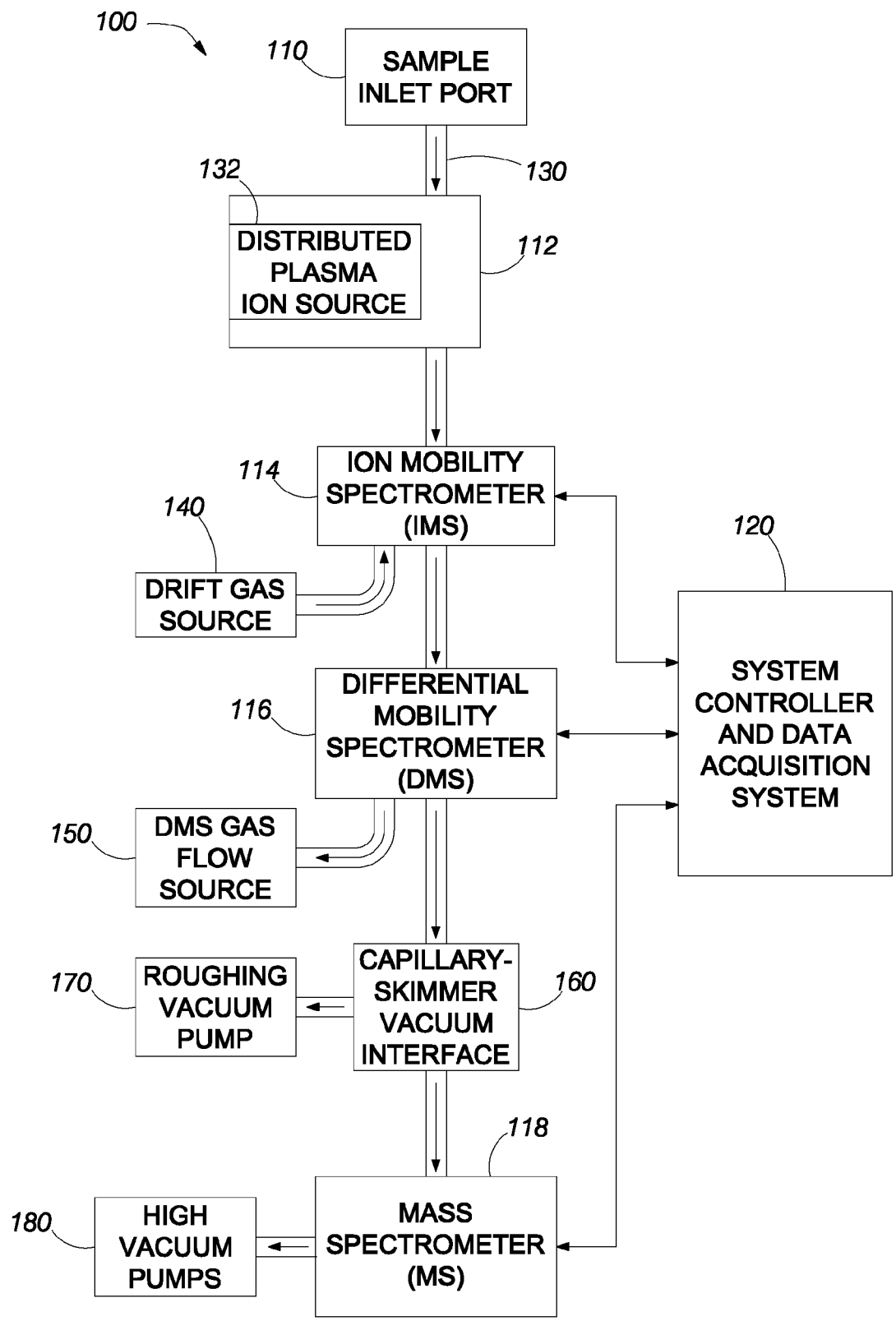
FIG. 1 illustrates a block diagram of a system for detecting trace amounts of chemical materials.
Figure 5:
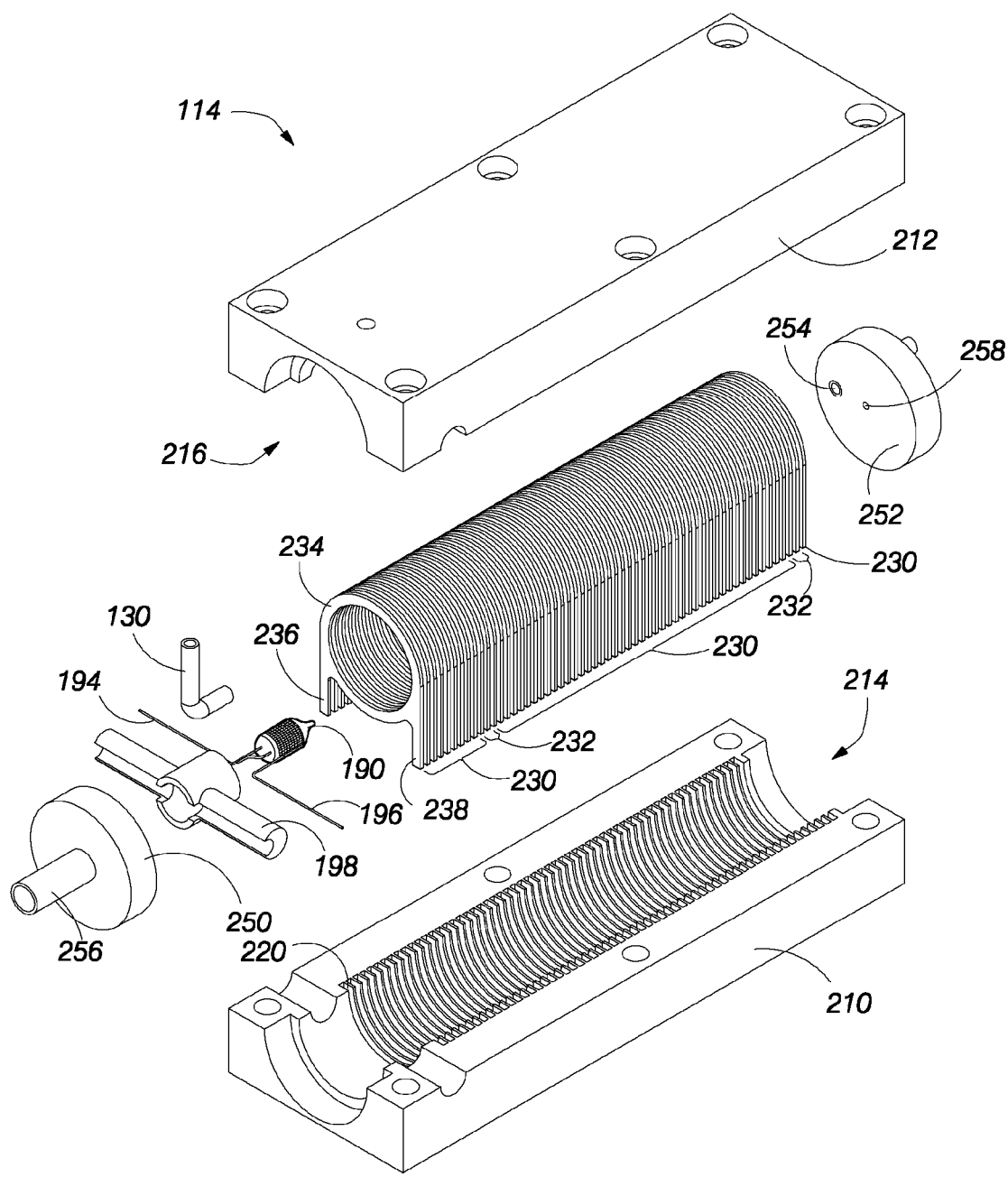
FIG. 5 illustrates an exploded perspective view of the IMS of FIG. 4.

FIG. 1 illustrates a block diagram of a system 100 for detecting trace amounts of chemical materials, such as, for example, explosives, contaminants and other target analytes of interest. The system uses atmospheric pressure ionization in both positive and negative ion modes to separate the molecules being analyzed. The system uses multidimensional orthogonal detection and analysis.

FIG. 2 illustrates a perspective view of an embodiment of the system 100 looking from the top. For illustration purposes, some of the components of the system 100 are not illustrated in one or both figures. As shown in FIG. 2, the system 100 comprises a first (upper) circuit board 102 and a second (lower) circuit board 104 that are attached to each other in a spaced apart configuration using conventional standoffs. The primary system components shown in FIG. 1 are mounted on the upper circuit board. The low voltage supplies and the digital circuitry (e.g., a system controller and associated control circuitry) are mounted on the second circuit board. For safety considerations, the high voltage power supplies (not shown) are secured to the bottom side of the first circuit board between the first circuit board and the second circuit board to physically isolate the high voltage supplies from inadvertent access by a person working on the components on the exposed side of either circuit board.

As shown in FIG. 1, the system 100 comprises a sample inlet port 110, an ionizer zone 112, a miniature ion mobility spectrometer (IMS) 114, a miniature differential mobility spectrometer (DMS) 116 and a miniature quadrupole array mass spectrometer (QAMS) 118. The system components are connected in tandem as illustrated in FIG. 1. As used herein, "tandem" refers to the sequential flow of the molecules and the ions from one component of the system into the next component of the system. As shown in FIG. 2, the physical embodiments of the components are not necessarily physically aligned such that each successive component follows the previous component. Although certain components of the system 100 in FIG. 2 are positioned in parallel with other components, the ions flow through the system components in the sequence illustrated in FIG. 1. The system 100 may also be implemented with other footprints.

The system 100 includes a system controller 120, which is advantageously a microcontroller or other programmable control device. The system controller 120 selectively enables the IMS 114, the DMS 116 and the QAMS 118 to operate in various modes that are described below. The system controller 120 also controls the timing of gates within the IMS 114, as described below.

Other circuits not shown and not described in detail herein, such as an IMS electrometer and a QAMS electrometer, are located on the opposite side of first circuit board 102 in proximity to the analyzers to reduce noise pickup. Similarly, the QAMS RF power supply is located proximate to the QAMS 118 analyzer in order to eliminate stray capacitances. The circuits are connected directly to the respective analyzers.

The sample inlet port 110 (not shown in FIG. 2) of the system has an inlet air flow from a source (not shown) of clean dry air at a suitable flow rate. The surface sample is positioned in the sample inlet port 110 so that sample particles and vapors are injected into the air flow. For example, the surface sample may be heated or exposed to radiant energy to release the particles so that the particles and vapors are transportable by the air flow. The particles and vapors exit the sample inlet port 110 via a passage 130, which is heated in preferred embodiments.

The sample particles and vapors are transferred to the ionization zone 112 where the particles and vapors are ionized by a distributed plasma ion source (DPIS) 132. The DPIS 132 is automatically switchable between a positive mode (e.g., to detect peroxide explosives such as TATP) and a negative mode (e.g., to detect NG and RDX) in accordance with a list of target explosives within the microcontroller 120. As further described below, the DPIS 132 and the surrounding ionization zone 112 are incorporated into one end of the IMS 114 in preferred embodiments.

After being ionized in the ionization zone, packets of ions are selectively gated into the drift tube of the IMS 114, which is configured as a two-gate IMS cell, described below. Within the IMS 114, the packets of ions are caused to propagate from the ionization zone 112 at a first end of the drift tube to a second end of the of the drift tube under the influence of an electrical field gradient. The field gradient is selected in accordance with the polarity of the ions being analyzed. The ions propagate through the drift tube of the IMS 114 against a drift gas provided by a drift gas source 140. The drift gas enters the second end of the IMS 114 and drifts through the drift tube of the IMS 114 toward the first end where the drift gas exits the IMS 114 at the second end. In particular, the IMS 114 includes an inlet gate and an outlet gate, which are described below. Briefly, the inlet gate enables a packet of ions to enter the draft tube within the IMS 114 and to propagate to the second end of the drift tube. By activating the outlet gate at a certain time within the IMS spectrum, ions of a particular mobility are selectively passed through the second end of the drift tube and exit the IMS 114 while the other ions are blocked.

Ions that pass through the outlet gate of the IMS 114 enter the DMS 116, which is positioned at an exit port of the IMS 114. In the DMS cell 116, the ions are excited in high frequency, high amplitude fields and are filtered by applying an appropriate compensation voltage (CV). The ions are moved pneumatically by establishing a gas flow within the DMS cell 116. For example, in the illustrated embodiment, the DMS 116 is positioned in one end of a manifold 150. The manifold 150 is positioned on the upper circuit board 102 so that the DMS 116 is positioned proximate an ion outlet of the IMS 114. A DMS gas flow is provided within the manifold 150 by a gas flow source 152 (e.g., a miniature fan), which is positioned at an opposite end of the manifold 150.

A capillary-skimmer vacuum interface 160 is positioned between the exit of the DMS cell 116 and the MS 118. As described in more detail below, the capillary-skimmer vacuum interface 160 comprises a heated capillary 162 having an input end secured within the manifold 152 and aligned with the exit of the DMS cell 116. The capillary extends to a skimmer 164 positioned proximate to the QAMS 118 in a vacuum manifold 166. Filtered ions exiting the DMS cell 116 are injected into the capillary-skimmer vacuum interface 160 and propagate to the QAMS 118. The capillary 162 is biased in order to efficiently sample ions at the exit of the DMS. A metal capillary, a glass-lined capillary or a glass capillary with metallized tips may be used to transport ions into the vacuum region. An advantage of a glass capillary is the ability to independently optimize the voltages on the inlet and the exit of the capillary.

The capillary-skimmer vacuum interface 160 comprises at least two pressure reduction (vacuum) stages that reduce the ambient pressure (e.g., approximately 760 Torr) to a pressure of about 1 milliTorr at which the QAMS 118 is operated. As described below, the first pressure reduction stage comprises a small chamber at the output end of the capillary 162, which is evacuated by a small roughing pump 170 via a pneumatic passage 172 (FIG. 2) to a pressure of approximately 1 Torr. The flow established inside the capillary 162 transports the ions to the capillary exit (e.g., the output end of the capillary) where the ions are subject to supersonic expansion.

The second pressure reduction stage is established using the orifice of the skimmer 164 (described below), which is properly located at a selected distance from the output end of the capillary 162. The skimmer orifice separates the small chamber from a second chamber that is maintained at a vacuum of approximately 1 milliTorr by a high vacuum pumping system 180. As shown in FIG. 2, the high vacuum pumping system 180 advantageously comprises a conduit 182 having a first end coupled to the vacuum manifold 166 around the QAMS 118. The second end of the conduit 182 is coupled to a high vacuum valve 184. The high vacuum valve 184 is normally closed and only opens when power is applied. When the high vacuum valve 184 is open, the vacuum manifold 166 is pneumatically connected to a getter pump 186 and an ion pump 188, which are activated to reduce the pressure in the second chamber to approximately 1 milliTorr. Although the getter pump 186 and the ion pump 188 have limited service lives, the sealing action of the high vacuum valve 184 retains a vacuum previously created within the two pumps such that pumps only have to remove ions and other molecules when the high vacuum valve 184 is opened when the system 100 is active. The valve 184 also serves to protect the two pumps from accidental overpressures that may require the pumps to be regenerated.

In the exemplary embodiment described herein, the distributed plasma ion source (DPIS) 132 in the ionization zone 112 of FIG. 1 is implemented by a non-radioactive ion source built by Transducer Technology Inc., a portion of which is illustrated in FIG. 3. The DPIS 132 is described in U.S. Pat. No. 7,157,721. The DPIS 132 provides a distributed or controlled volume of plasma as an alternative to point-to-point corona or radioactive ionization sources in ion detection instruments. The DPIS 132 is classified as a "modified dielectric barrier discharge source." The DPIS 132 is miniature and is constructed to meet requirements for longevity, durability, and repeatability. The DPIS 132 is supplied with a DC input voltage in a range of 12 volts to 18 volts from a conventional voltage source (not shown). The DPIS 132 includes a voltage generator (not shown) that is controlled to provide a DC extraction voltage of the same polarity as the desired ions in a range from 0 volts to ±2000 volts. The DPIS 132 draws less power (less than 3.5 watts) than a corona discharge source and is more stable. Output ion current measured as a function of the extraction voltage for different input voltage values shows an ion current 10 times higher than that obtained with radioactive sources.

The DPIS of FIG. 3 operates at atmospheric pressure by placing a high RF voltage across two overlapping electrodes separated by a dielectric medium. With two electrodes, preferably of dissimilar size attached to opposite sides of a thin dielectric, a suitable high-voltage AC signal across the electrodes produces a high electric field along the entire edge of the smaller electrode. The high electric field ionizes the gas sample, and creates the resulting plasma. In the illustrated embodiment, the DPIS 132 comprises a cylindrical glass bulb 190 about the size of a small neon bulb, with the small electrode (not shown) inside the bulb 190 and with the larger electrode advantageously comprising a wire mesh 192 formed around the outside of the glass. The inner electrode and the wire mesh 192 are coupled to the voltage generator (not shown) via a first conductor 194 and a second conductor 196, respectively. The bulb 190 is held by a support structure 198 that is fixed in a location close to the first end of the IMS 114, as discussed below.

The shape and the circumference of the smaller electrode of the ion source of FIG. 3 controls the quantity of plasma that is produced. The ionized molecules formed by the ion source are dependent upon the reaction region configuration. As monitored by a mass spectrometer, several reaction region configurations yield ions that are similar to those generated in a corona discharge. The positive ions produced by the ion source are similar to the positive ions generated by $^{63}$Ni, $^{273}$AM, or by corona discharge. The negative ions produced by the ion source are similar to the negative ions generated by a point-to-point corona discharge except that the reaction region configuration aids in discriminating between the formation of $NO_3^-$, $CO_3^-$, and $O_2^-$ ions. The DPIS 132 of FIG. 3 is located in a confined but not airtight volume, which is typically 1 inch long by 0.5 inch in diameter. The reactions within the volume lead to the formation of $NO_3^-$ ions, while an open configuration, such as a conventional open corona ion source, shows a predominant ion as $CO_3^-$ with minor ions of $O_2^-$ and $O_3^-$. In the illustrated embodiment, the DPIS 132 is located in the IMS 114 proximate to the first end of the drift tube, as described below.

FIGS. 4-10 illustrate an embodiment of the IMS 114. FIG. 4 illustrates the IMS 114 coupled to the DMS 116 within the manifold 152. As illustrated, the IMS 114 comprises a base 210 and a top cover 212 that are secured together when the IMS 114 is assembled. As shown in exploded view of FIG. 5, the upper surface of the base 210 has a semicircular bore 214 formed longitudinally from a first end to a second end. The top cover 212 has a matching semicircular longitudinal bore 216 so that the two semicircular bores 214, 216 form a circular bore through the IMS 114 when the base 210 and the top cover 212 are attached. As further shown in FIG. 5, a plurality of semicircular grooves 220 are formed in the circular bore at equally spaced intervals from a location displaced from the first end to a location displace from the second end. For example, in the illustrated embodiment, the base 210 includes 58 semicircular grooves between the two ends. The top cover 212 includes a corresponding plurality of grooves (not shown) that are aligned with the grooves 220 in the base 210.

Figure 6:
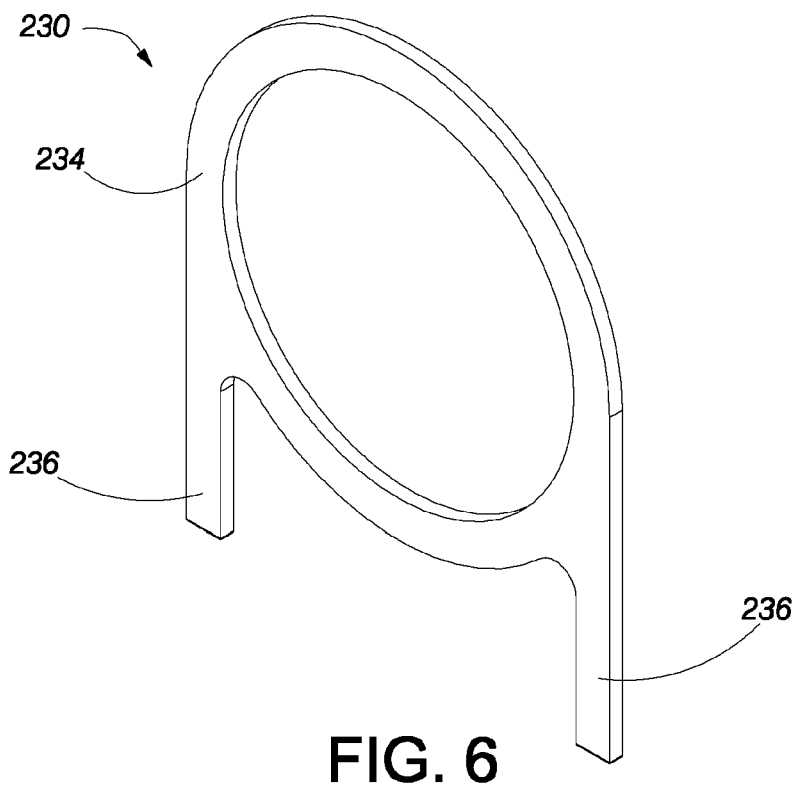
FIG. 6 illustrates an enlarged perspective view of one of the wicket-shaped conductors of FIG. 5.
Figure 7:
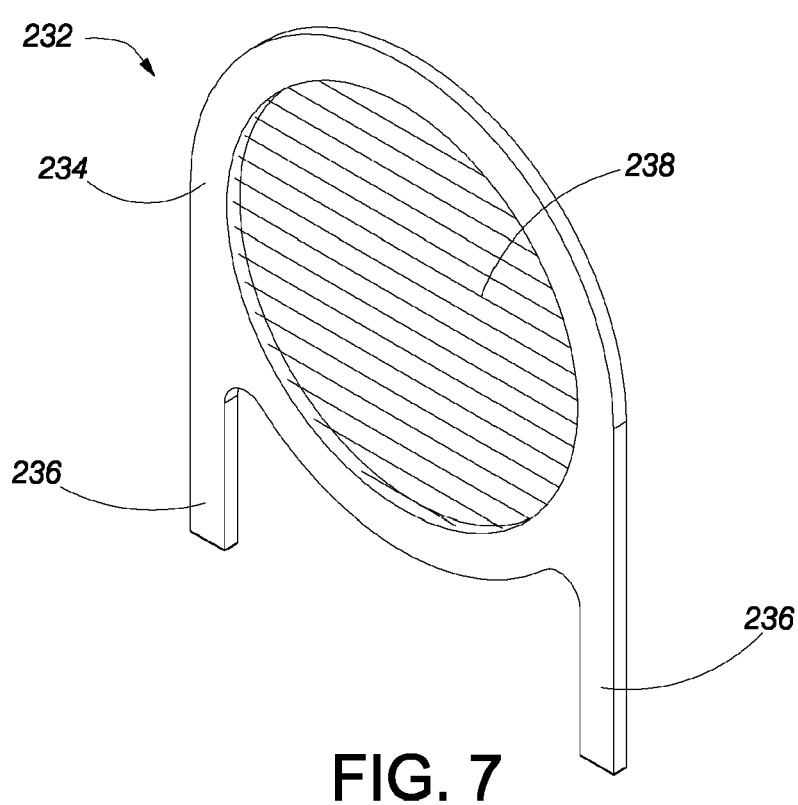
FIG. 7 illustrates an enlarged perspective view of one of the wicket-shaped conductors of FIG. 5 with the wire mesh to enable the conductor to be used in a Tyndall ion gate.
Figure 8:
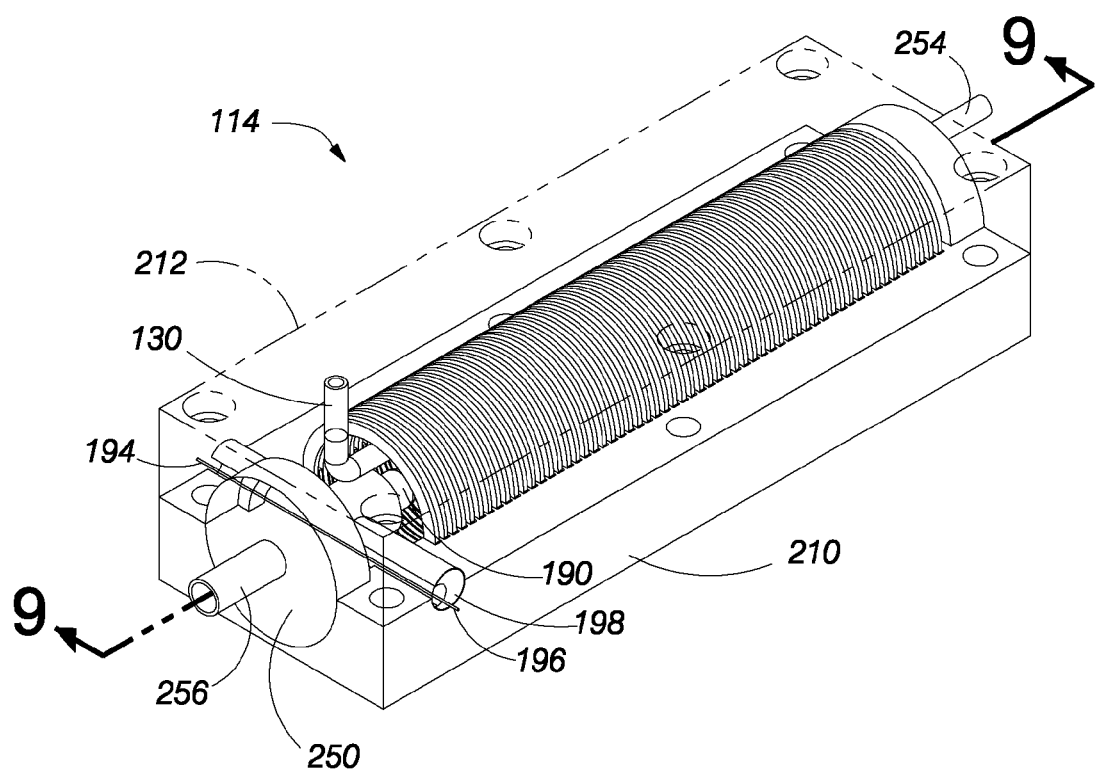
FIG. 8 illustrates a perspective view of the IMS of FIG. 4 with the top cover show in phantom to show the placement of the internal components.
Figure 9:
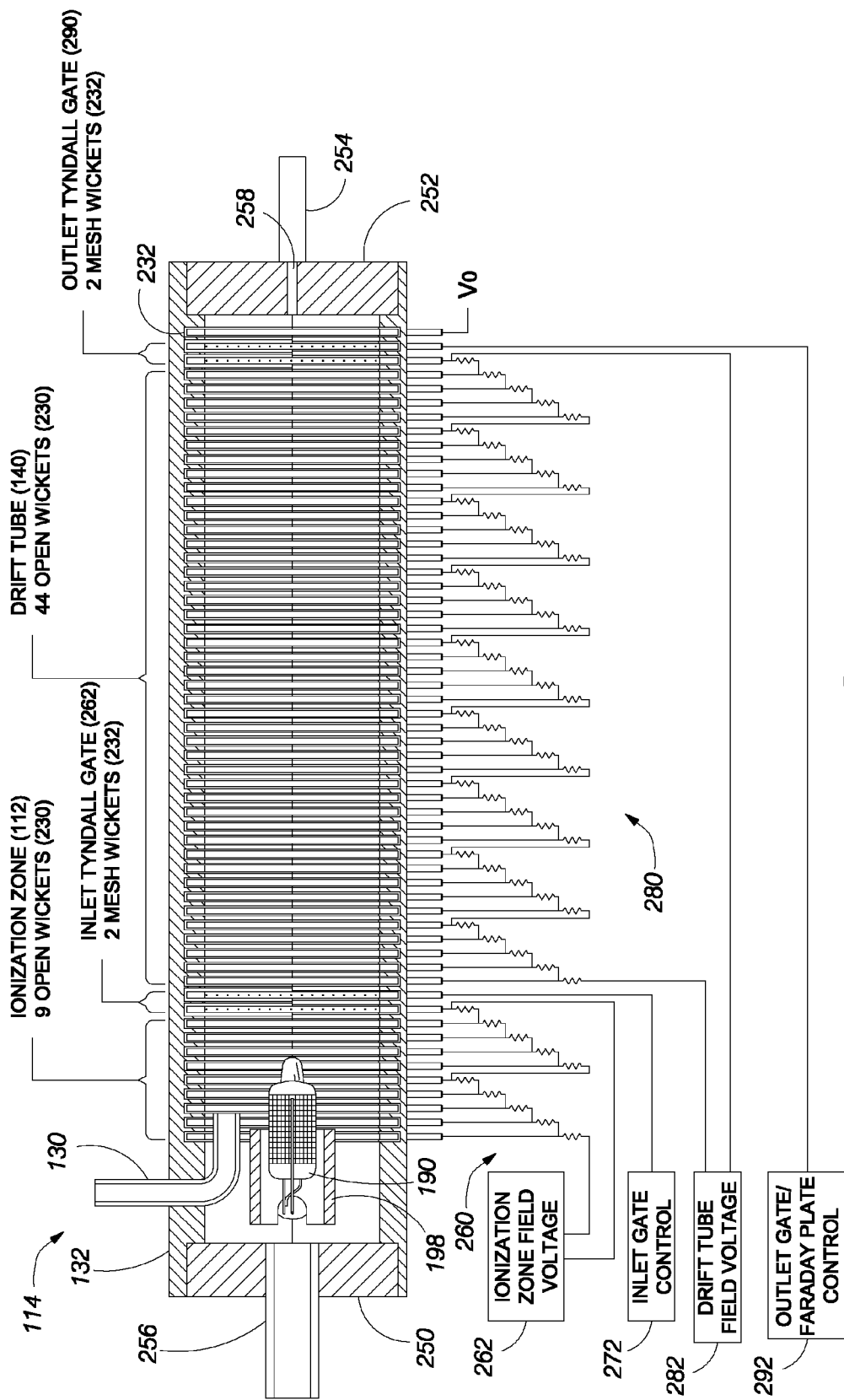
FIG. 9 illustrates a cross-sectional view of the IMS of FIG. 4 taken along the line 9-9 in FIG. 8 and further showing a schematic representation of the resistor networks that provide the electric field distribution along the drift tube.
Figure 10:
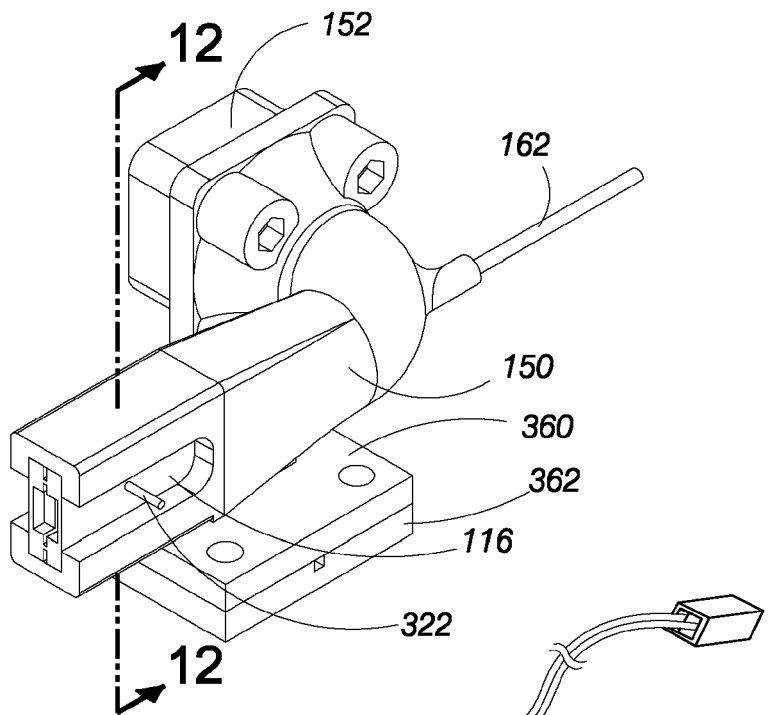
FIG. 10 illustrates an exemplary differential mobility spectrometer (DMS) used in the system of FIGS. 1 and 2 and further illustrates the support manifold that produces pneumatic pressure to cause ions to flow through the DMS.
Figure 11:
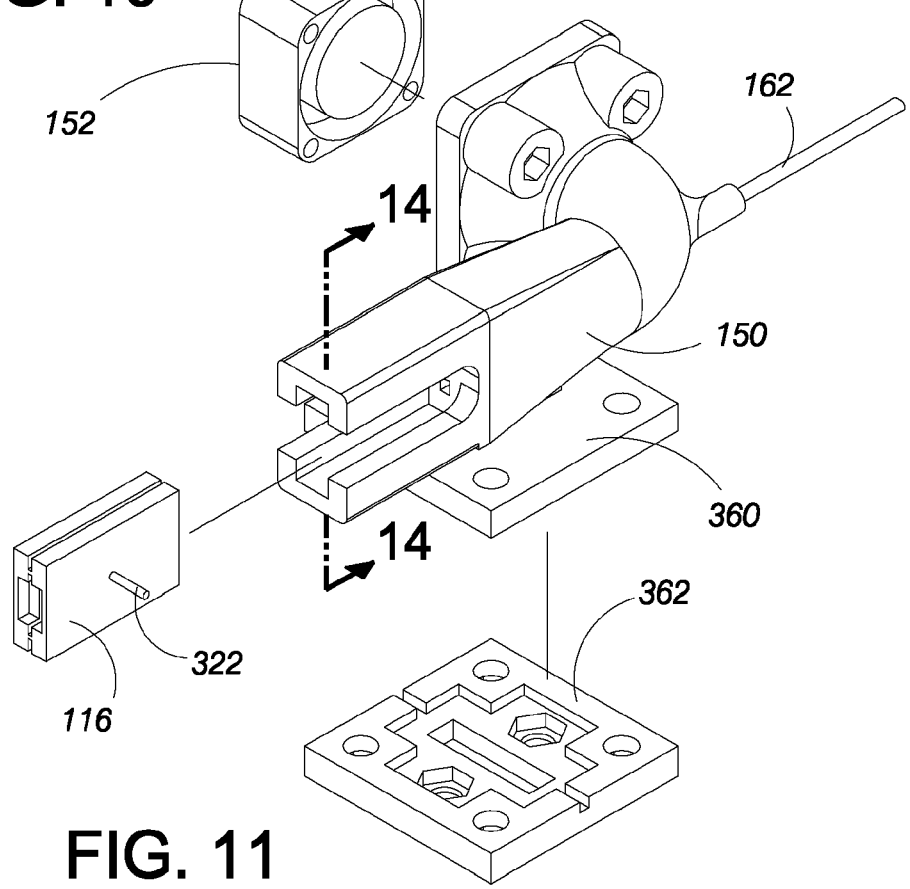
FIG. 11 illustrates an exploded view of the DMS and the support manifold of FIG. 10.

The grooves 220 in the base 210 and the corresponding grooves in the top cover 212 support a corresponding plurality of wicket-shaped conductors. In particular, the grooves 220 support 54 wicket-shaped conductors 230 of a first type shown in more detail in FIG. 6 and support 4 wicket-shaped conductors 232 of a second type shown in more detail in FIG. 7. As shown in FIGS. 6 and 7, each wicket-shaped conductor 230, 232 comprises a circular ring 234 having an outside diameter of approximately 1 inch and having an inside diameter of approximately 0.83 inch. The conductors have a thickness of approximately 0.03 inch. Each wicket-shaped conductor 230, 232 has two legs 236 that extend tangentially downward from the ring 234. Each semicircular groove 220 in the base 210 includes a pair of holes (not shown) that extend through the base 210 so that a portion of each leg 236 extends below the bottom surface of the base 210, as shown in FIG. 10. The wicket-shaped conductors 230, 232 preferably comprise nickel-plated, stainless steel that facilitates soldering the rings to other components, such as grid wires for gates, resistors, and the like.

As shown in FIG. 6, the area within the inner circumference of the ring 234 in the wicket-shaped conductor 230 of the first type is open. In contrast, as shown in FIG. 7, the area within the inner circumference of the ring 234 in the wicket-shaped conductor 232 of the second type is traversed by a plurality of grid wires forming a mesh 238. In the illustrated embodiment, the mesh 238 comprises 17 generally horizontal grid wires, which are spaced apart from each other across the inner area of the ring 234 at a distance of approximately 0.05 inch. The grid wires 238 advantageously comprise nickel-plated stainless steel and have diameters of approximately 0.01 inch When the wicket-shaped conductors 230 are positioned in the grooves 220 as shown, the rings of the conductors 230 form a drift tube 240 a first gate 242 and a second gate/detector 244 of the IMS 114. The inside diameters of the rings and the non-grooved portions of the semicircular bores 214, 216 form the drift tube 240 with a substantially continuous inner wall between a first end cap 250 and a second end cap 252. The drift tube 240 directs the flow of the counter-flowing drift gas that enters the second end of the IMS 114 via a drift gas inlet tube 254 formed in the second end cap 252. The drift gas exits the IMS 114 via a drift gas outlet tube 256 formed in the first end cap 250. As discussed below, the ions created in the ionization zone 112 travel electrostatically toward the second end cap 250 and exit via an ion exit port 258 formed substantially in the middle of the second end cap 250.

The portions of the legs of the wicket-shaped conductors 230 that extend through the base 210 are electrically connected to circuitry on the upper circuit board 102, as discussed below. Preferably, the base 210 and the top cover 212 include integral heating elements, which heat the drift tube 240 to a temperature of, for example 150 degrees C. The base comprises 0.125-inch thick glass reinforced epoxy laminate, such as, for example, Macor® FR 4, available from Corning Corporation, or another material suitable for elevated temperatures (e.g., a ceramic material such as alumina). The base is perforated with evenly spaced holes to provide approximately 0.070-inch spacing between the conductors that are inserted in the holes. Thus, the drift tube 240 comprising 58 wicket-shaped conductors has an overall length of less than 10 centimeters. The overall length of the IMS 114 between the two end caps 250, 252 is approximately 12.5 centimeters.

The first nine wicket-shaped conductors 230 (at the left end in FIGS. 5, 7 and 8) of the IMS 114 are associated with the ionization region 112 and are positioned proximate the ion source (DPIS) 132. In particular, the DPIS 132 extends into the portion of the drift tube 240 defined by the first nine conductors 230 The first nine wicket-shaped conductors 230 are interconnected via first resistor network 260 across a ionization zone field voltage source 262 to provide an electric field across the first nine conductors of approximately 200 volts/centimeter.

The next two wicket-shaped conductors 232 in the IMS cell comprise a first Tyndall ion gate 270, which corresponds to the IMS inlet gate discussed above. As discussed above, the conductors 232 include the grid wires 238 shown in FIG. 7. In the illustrated embodiment, the upstream conductor 232 in the first Tyndall ion gate 270 is connected to the first resistor network 260 via a respective resistor. As discussed below, the voltage on the downstream conductor 232 in the first Tyndall ion gate 270 is controlled by an inlet gate control circuit 272 and is varied with respect to the voltage on the upstream conductor 232 to open and close the gate.

The next 44 wicket-shaped conductors 230 after the first Tyndall ion gate 270 comprise the main body of the drift tube 240 of the IMS 114. The 44 wicket-shaped conductors 230 are electrically interconnected by a second resistor network 280 across a drift tube field voltage source 282 to provide an evenly distributed field of approximately 200 volts/centimeter.

The 44 conductors 230 in the main body of the drift tube 240 are followed by two wicket-shaped conductors 232 with grids, which are connected as a second Tyndall ion gate 290, which corresponds to the IMS outlet gate discussed above. In the illustrated embodiment, the upstream conductor 232 in the second Tyndall ion gate 290 is connected to the second resistor network 280 via a respective resistor. As discussed below, the second Tyndall gate 290 also advantageously functions as a Faraday plate in one operational mode of the IMS 114. The downstream conductor 232 in the second Tyndall ion gate 290 is controlled by an outlet gate/in situ Faraday plate gate control circuit 292.

The last wicket-shaped conductor 230 (at the right in FIGS. 5, 8 and 9) completes the overall electric field distribution across the drift tube 240. The lowest voltage Vo in the electric field distribution is applied to the last wicket-shaped conductor.

The voltage Vo is selected as an optimum voltage for the DMS 116, which follows the IMS 114. For example, in one embodiment, the voltage Vo is in a range of 0 volts to 30 volts. The voltage Vmax applied to the wicket-shaped conductor 230 at the inlet end of the drift tube 240 is the maximum voltage applied across the drift tube and has a magnitude of approximately 3,000 volts. The drift voltage is dropped to Vo in 44 equal steps using a voltage divider constructed from 1-megohm or 2-megohm precision resistors. The resistance is selected in accordance with the current capacity of the high voltage supply.

As discussed above, the wicket-shaped conductors 232 with the wire mesh 238 operate as Tyndall gates to control the flow of ions through the drift tube 240. The "upstream" wicket/conductor in each Tyndall ion gate (e.g., the respective wicket-shaped conductor 232 in each gate closer to the ion source) is held at a selected fixed voltage corresponding to the position of the gate in the electrical field distribution. The voltage applied to the "downstream" wicket-shaped conductor 232 in each Tyndall ion gate is varied to selectively open and close the respective gate. The gate is closed by applying a voltage to the downstream wicket-shaped conductor 232 that is higher than the upstream drift ring voltage by a magnitude of approximately 0.01×Vmax (e.g., approximately 30 volts greater when Vmax is 3,000 volts). The gate is opened by applying a voltage that is lower than the upstream drift ring voltage by approximately 0.01×Vmax (e.g., approximately 30 volts less when Vmax is 3,000 volts). In order to control the flow of negative ions, the polarities of the previously discussed voltages are reversed. Gate opening and closing pulses supplied by the instrument electronics should have rise times and fall times of no more than 1 microsecond.

The downstream mesh of the second Tyndall ion gate 290 is also electrically connectable by the outlet gate/Faraday plate control circuit 292 to selectively function as a Faraday plate to measure the IMS spectrum when the IMS is operating in the open (high sensitivity) mode. In this mode, the control wire of the grid is attached to a current-to-voltage converter (not shown) capable of measuring picoamps. In order to measure current at this low level, the mesh is isolated from ground by about 10 gigaohms or more. This isolation is provided within the drift tube assembly and within any electronics attached to the control wire.

In alternative embodiments, the downstream mesh of the second Tyndall ion gate 290 may be connected to a fixed voltage potential and the voltage on the upstream mesh may be switched as described above to open and close the second Tyndall ion gate 290. In further alternative embodiments, either Tyndall ion gate may be replaced with a Bradbury-Neilsen gate (BNG).

FIGS. 10-15 illustrate an embodiment of the parallel plate DMS 116 within the manifold 150. The DMS 116 is constructed using a flat plate design with parallel geometry. The parallel geometry offers several advantages including ease of manufacturing and superior resolution.

Figure 12:
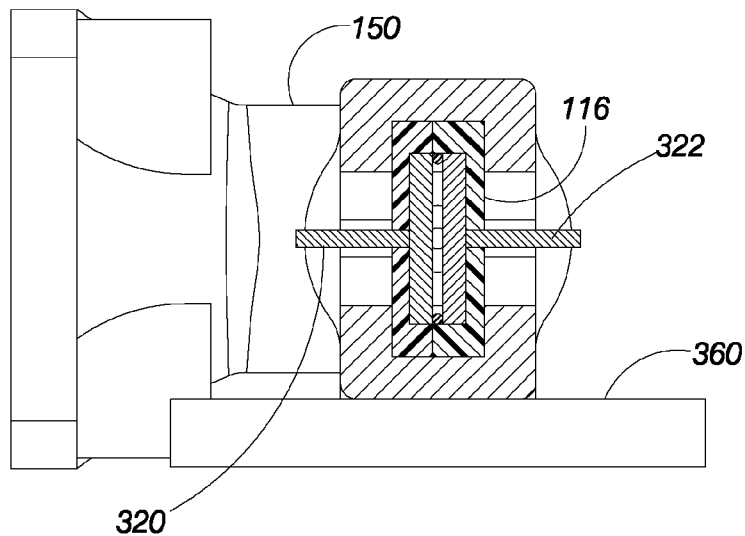
FIG. 12 illustrates a cross-sectional view of the DMS in the support manifold taken along the line 12-12 in FIG. 10.
Figure 13:
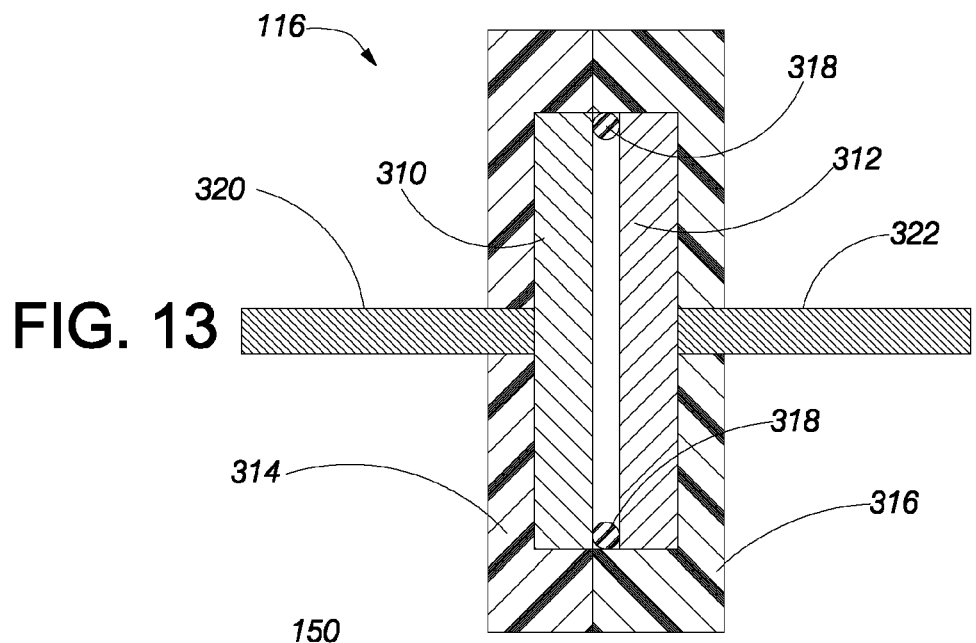
FIG. 13 illustrates an enlarged cross-sectional view of the DMS of FIG. 12.
Figure 14:
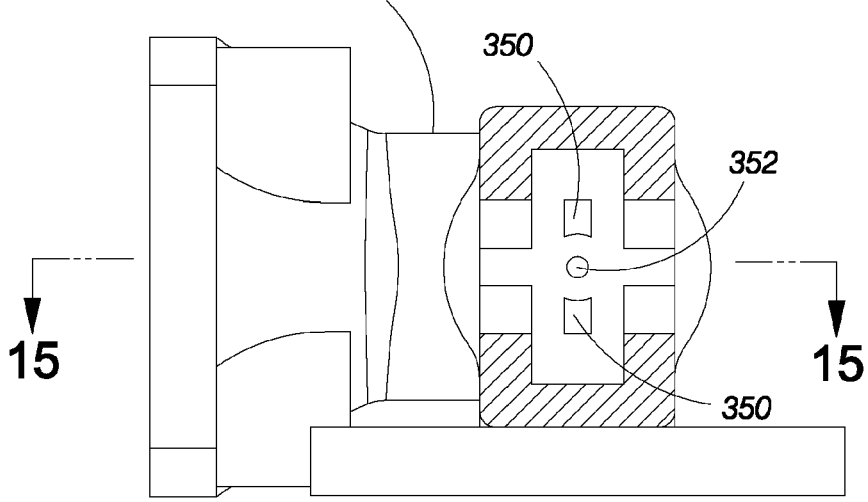
FIG. 14 illustrates a cross-sectional view of the support manifold of FIGS. 11 and 12 taken along the line 14-14 in FIG. 12.

As shown in the cross-sectional views in FIGS. 12 and 13, the geometry of the DMS 116 comprises a first stainless steel plate 310 and a second stainless steel plate 312, which is parallel to the first plate 310. Each plate 310, 312 has a width of approximately 5 millimeters, a length of approximately 15 millimeters and a thickness of approximately 1 millimeter. The first plate 310 is encased and recessed in a first PEEK (polyetheretherketone thermoplastic) support 314, and the second plate 212 is encased and recessed in a second PEEK support 216. The PEEK supports 314, 316 provide mechanical stability and electrical insulation for the plates.

Each PEEK support 314, 316 has a width of approximately 8 millimeters and a length of approximately 8 millimeters. In the illustrated embodiment, the first PEEK support 314 has a thickness of approximately 2 millimeters and has a recess in a face that has a depth of approximately 1 millimeter so that a face of the first steel plate 310 is flush with the face of the first peek support 314. The second PEEK support 316 has a thickness of approximately 2.5 millimeters and has a recess in a face that has a depth of approximately 1.5 millimeters so that a face of the second steel plate 312 is recessed by approximately 0.5 millimeter with respect to the face of the second PEEK support. Preferably, each plate 310, 312 is secured in the recess of the respective PEEK support by high temperature epoxy or other suitable adhesive.

The DMS 116 further includes a pair of substantially incompressible silica or polymer spacer rods 318 positioned between the two stainless steel plates 310, 312 to maintain the two steel plates a fixed distance (e.g., 0.5 millimeter) apart when the two PEEK supports are fastened securely together (e.g., with conventional fasteners (not shown) such as screws). Electrical connections to first and second plates 310, 312 are made via respective first and second electrode wires 320, 322 through holes in the respective PEEK supports 314, 316. The electrode wires are spot-welded to the respective plates prior to inserting the plates into the recesses in the PEEK supports. The top and bottom plates are secured to each other through the PEEK supports and the insulating polymer with four screws to ensure mechanical stability and alignment. After assembly, the DMS cell 116 is inserted into the end of the manifold 150 and is secured by compression and by a non-conductive tape.

Figure 15:
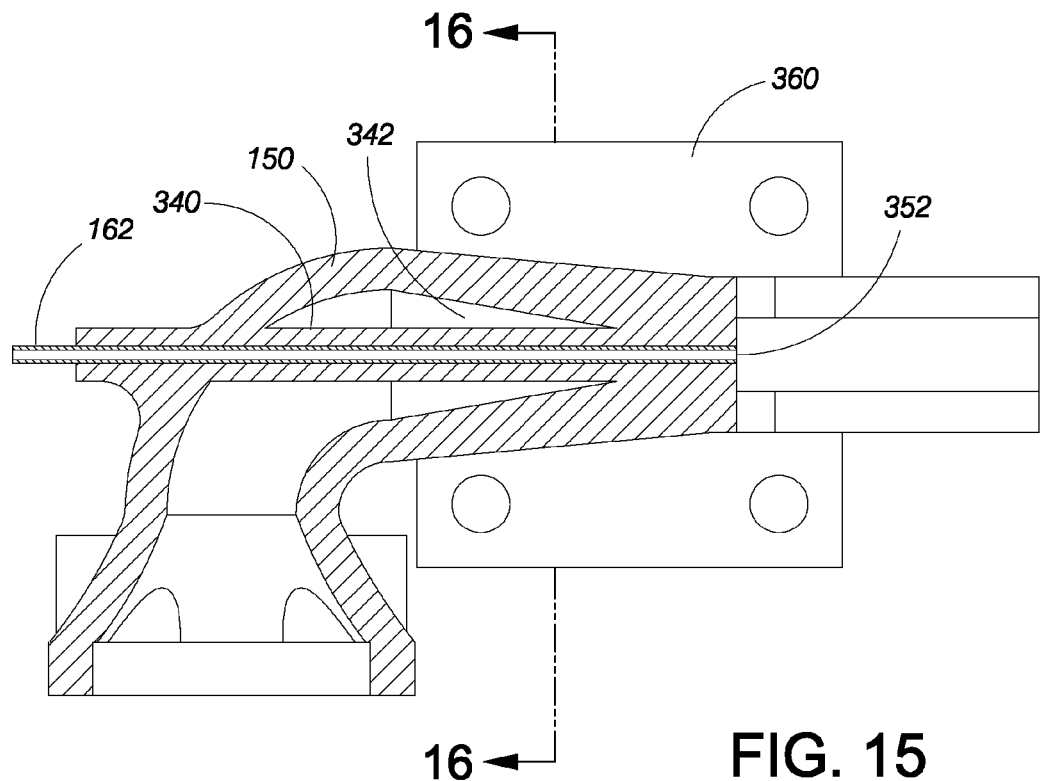
FIG. 15 illustrates a cross-sectional plan view of the support manifold of FIGS. 10 and 11 taken along the line 15-15 in FIG. 14.
Figure 16:
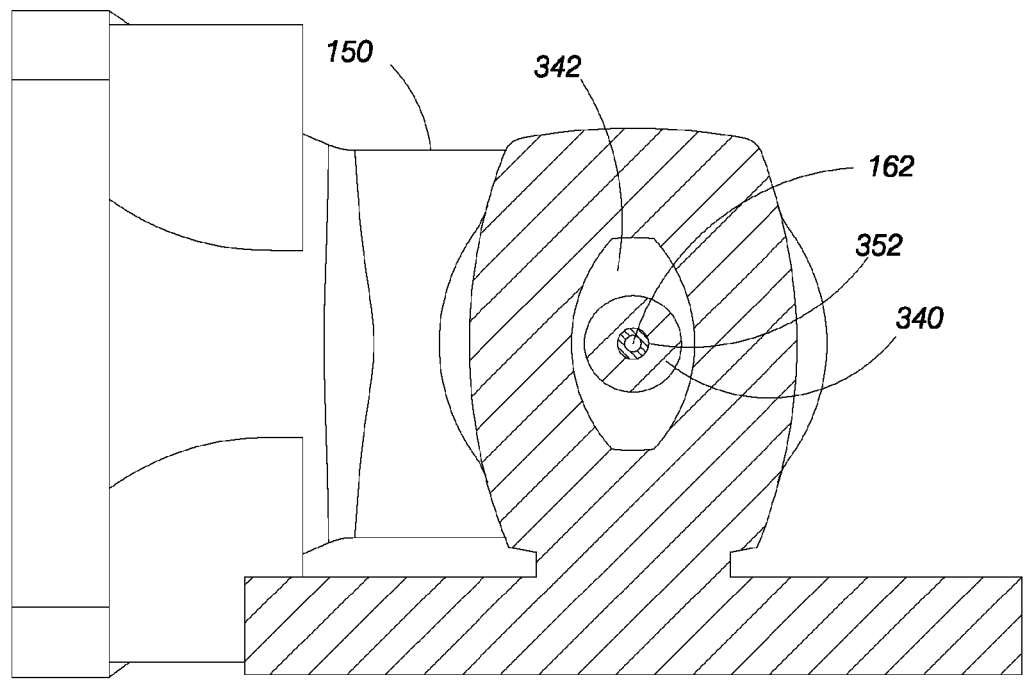
FIG. 16 illustrates a cross-sectional view of the support manifold of FIGS. 10 and 11 taken along the line 16-16 in FIG. 15.

The hybrid support manifold 150 also supports one end of the capillary 162 within a cylindrical capillary support 340 as best shown in the plan view cross section in FIG. 15. The fan 152 at the opposite end of the support manifold 150 creates a pressure drop within a cavity 342 that surrounds the cylindrical support. The cavity 342 tapers from a relatively large cross-sectional area at the fan 152 to a relatively small cross-sectional area where the cavity 342 terminates in a pair of portals 350 that are aligned with the 0.5-millimeter space between the two plates 310, 312 in the DMS cell 116. As illustrated in FIGS. 15 and 16, the relatively low flow velocity of the fan 152 over a relatively large cross-sectional area is gradually concentrated in the tapering cavity 342 to a relatively high flow velocity through the small portals 350. The increased flow velocity causes a sufficient pressure drop to pneumatically transport the ions across the plates 310, 312 from the ion exit port 258 of the IMS 114. As shown in the cross-sectional views in FIGS. 14 and 15, the end of the capillary 162 is exposed at a bore 352 between the two portals 350. Thus, the end of the capillary 162 is aligned with the center of the outlet of the DMS cell 116. Thus, the capillary 162 receives a flow of ions from the region of highest ion concentration in the DMS cell 116.

The hybrid support manifold 150 includes an upper base structure 360, which is removably secured to a matching lower base structure 362. In the illustrated embodiment, the lower base structure 362 is attached to the upper circuit board 102 in a fixed position with respect to the position of the IMS 114. Thus, when the upper base structure 360 of the hybrid support manifold 150 is attached to the lower base structure 362, the DMS cell 116 in the hybrid support manifold 150 is accurately aligned with the ion exit port 258 of the IMS 114.

In one embodiment, the capillary 162 has an inside diameter of approximately 250 microns. The capillary 162 may comprise an electrically conductive metal or the capillary 162 may comprise glass. Preferably, in embodiments using a glass capillary, the capillary 162 has metal tips so that a respective voltage can be applied to each end of the capillary to match the voltage of the other system components at each end.

Figure 17:
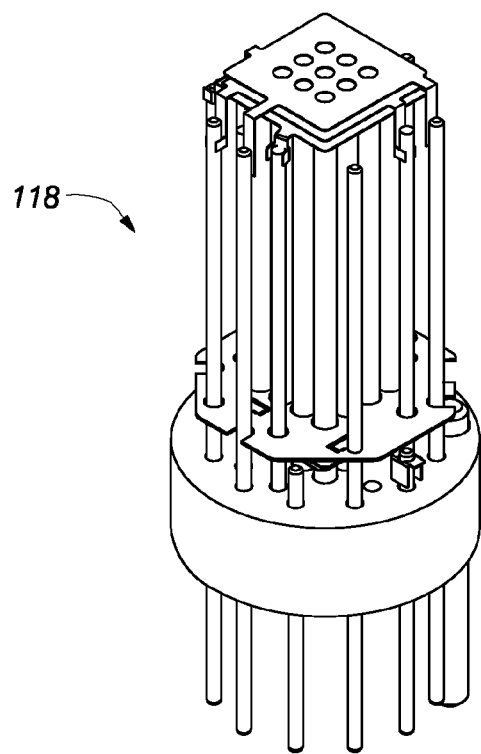
FIG. 17 illustrates a perspective view of an exemplary quadrupole array mass spectrometer (QAMS) used in the system of FIGS. 1 and 2.

FIG. 17 illustrates a perspective view of an exemplary miniature QAMS 118 that may be used in an embodiment of the system 100. For example, the QAMS 118 is advantageously a 30-millimeter quadrupole array.

Figure 18:
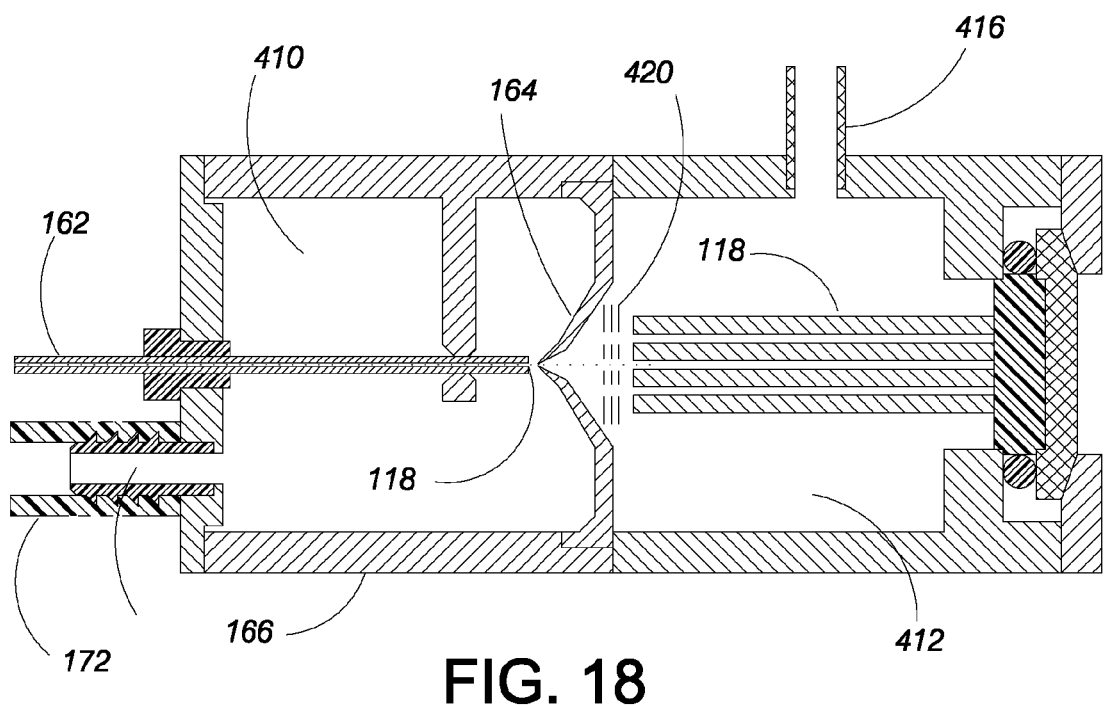
FIG. 18 illustrates a simplified cross-sectional view of the vacuum manifold of FIG. 2 to show the position of the end of the capillary with respect to the skimmer and the position of the skimmer with respect to the QAMS.

FIG. 18 illustrates a cross-sectional representation of the vacuum manifold 166 that comprises a first low vacuum stage (or chamber) 410 that is evacuated by a roughing pump (not shown) to a pressure of approximately 1 Torr and a second high vacuum stage (or chamber) 412 that is evacuated by the high vacuum pumping system described above to a pressure of approximately 1 milliTorr. In particular, the first stage 410 includes an evacuation port 414 that is coupled to the conduit 172 of FIG. 2, which is coupled to a roughing pump. The second stage 412 includes an evacuation port 416, which is coupled to the vacuum valve 184 via the conduit 182, as illustrated in FIG. 2. The QAMS 118 is positioned in the high vacuum chamber 412 of the vacuum manifold 166. The skimmer 164 separates the high vacuum chamber 412 from the lower vacuum chamber 410.

Ions exiting the DMS 116 described above are transferred through the pneumatic funnel provided by the support manifold 150 and enter the first end of the capillary 162. The capillary 162 transfers the ions into the first vacuum stage (e.g., the low vacuum chamber 410 of FIG. 18). The pressure in the first vacuum stage of approximately 1 Torr is established using the miniature roughing pump, which advantageously is a multistage trochoidal vacuum pump such as described in pending U.S. patent application Ser. No. 11/765,954 filed on Jun. 20, 2007, for Multi-Stage Trochoidal Vacuum Pump, which is incorporated herein by reference. The vacuum provided by the roughing pump causes a viscous flow within the capillary that moves the ions. The gasses experience a jet expansion at the exit end of the capillary 162. The skimmer 164 has a suitable diameter and proximity to the exit end of the capillary 162 that enables the skimmer 164 to efficiently sample the core of the gasses emanating from the capillary 162. The opening in the skimmer 164 is the orifice into the high vacuum stage (e.g., the second chamber 412 of FIG. 18). The skimmer 164 is positioned to place the orifice to the high vacuum stage in the region of free expansion after the ions exit the capillary 162 and before the location of the Mach disk. The position of the skimmer 164 is selected to avoid creating standing pressure waves that broaden the beam of ions of interest. Upon entering the high vacuum stage 411 after passing through the skimmer 164, the ions are focused into the quadrupole array 118 using a set of electrostatic lenses 420.

The ions are efficiently transmitted through the vacuum interface notwithstanding the small dimensions of the capillary 162 and the low vacuum pumping capacity. Using simple area ratios, the sampling efficiency of a uniform plume of ions that have dispersed over a 25-millimeter diameter area (based on the traditional spray outside diameter with respect to the ions that would be sampled into the small diameter capillary bore (e.g., an inside diameter of approximately 0.2 millimeters) is about 0.008% or 8 per 100,000 ions. However, the capillary inlet described herein is coupled to receive the ions that are exiting the DMS 116, and the ion source is no longer a dispersive source. Instead, the ion source is rather constrained and directional. Thus, the multiple order-of-magnitude ion loss encountered by traditional capillary sampling is greatly reduced. In further preferred embodiments, the ions exiting the DMS 116 are tailored to a small extent to further increase the capillary sampling efficiency. Since the DMS 116 presents a directed ion beam (e.g., a beam that is approximately 5 millimeters wide by 0.5 millimeters high) towards the capillary, the ion sampling efficiency is expected to be 0.31% or approximately 3 per 1,000; a factor of 37 gain without assistance from flow or electrostatic fields.

The geometry of the capillary-skimmer region contributes significantly to the efficient transfer of the ions into the high vacuum chamber 412. The skimmer 164 efficiently samples the central "core" of the expanding gasses emanating from the capillary 162, which separates atmospheric pressure from the first vacuum stage (the low vacuum chamber 410). The central core of the expanding gas contains the gaseous species of interest—the molecular species of greatest mass with respect to normal atmospheric constituents. The diameter of the skimmer 164 and proximity to the end of the capillary 162 is a function of the desired sampling efficiency versus the neutral gas load that can be supported in the second vacuum stage 412. In order to efficiently sample the expanding gas, the jet expansion character of the gasses exiting the capillary is preserved and the skimmer orifice is placed before the Mach disk (e.g., the location of the shock wave caused by the expanding gas reaching supersonic velocity). The conical feature of the skimmer 164 is configured so that the skimmer does not negatively affect the free expansion that occurs in the low vacuum stage 410. The skimmer 164 is configured and positioned to place the orifice to the second vacuum stage 412 in the free expansion after the capillary and before the Mach disk, and to do so without creating standing pressure waves that broaden the beam of ions of interest exiting the capillary.

The location $X_m$ of the Mach disk can be calculated in accordance with the following equation:

$$X_m/D = 0.67(p_0/p_1)^{1/2}$$

where:
D is the inside diameter of the capillary;
$p_0$ is the upstream pressure
$p_1$ is the downstream pressure
For a system going from $P_0=760$ Torr to $p_1=1$ Torr, the Mach disk lies 19 nozzle diameters away from the end of the capillary 162. Thus, for 0.1-millimeter diameter nozzle, the Mach disk lies 1.9 millimeters away from the end of the capillary. Ratios of skimmer distances to nozzle diameter of around 4.5 are reported in the literature and are used successfully with capillaries with an inside diameter of 0.7 millimeter. Thus, the illustrated embodiment of the system is implemented with a skimmer distance of 0.9 millimeter from the end of the capillary 162 based on a capillary having an inside diameter of 0.2 millimeter. This skimmer distance is acceptable although the capillary end is not a true nozzle.

A skimmer orifice diameter of 14% to 25% larger than the inside diameter of the capillary is recommended in preferred embodiments; however, the skimmer orifice diameter can be even larger if the vacuum pump for the second vacuum stage (e.g., the high vacuum stage) can handle the gas load. Thus, a skimmer 164 having an inside diameter in a range from 0.11 millimeter to 0.13 millimeter at 4.5 nozzle diameters from the end of the capillary 162 has a sufficient size to efficiently transport the ions exiting the capillary into the second vacuum stage. The skimmer 164 is electrically conductive because the skimmer is used to set the "birth" energy of the ions as they enter the second vacuum stage and the mean free path traveled by each ion increases. The skimmer 164 also dissipates space charge from the entering ion beam. The skimmer cone in the present embodiment does not need to be tapered as is often done with skimmers used for studying beam dynamics. The skimmer 164 operates properly with the angle of the skimmer cone set at 90 degrees or more. This angle enables better positioning of ion extraction electrostatic lenses in the back side of the skimmer and provides better conductance for the expanding gasses to dissipate before the filter.

As the ions and neutral gas pass through the skimmer 164, the pressure decreases rapidly. At some point past the skimmer orifice, an ion undergoes its last collisional dampening. At this last point of collision, the ion assumes a translational energy set by the electrical field gradient. Thus, the back side of the skimmer 164 operates as a lens to establish this electric field gradient.

A second lens element (not shown) may be advantageously placed within the expanding cone of the skimmer to narrow the energy spread where the ions assume their translational energy. The second lens is a conical lens that may also be a pressure barrier (e.g., a larger skimmer) that minimizes gases that are diverted in front of the second lens when entering the mass filter. The second lens works well when the vacuum pump is located in the front part of the second vacuum stage.

Figure 28:
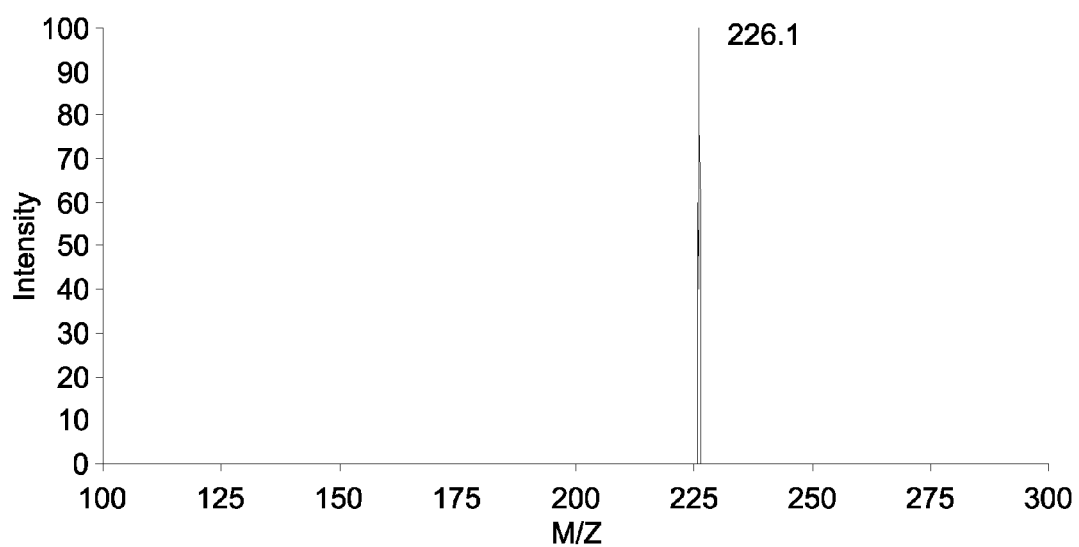
FIG. 28 illustrates a mass spectrum resulting from a two-gate IMS-DMS CV scan of a sample of TNT at 5 parts per million.

With a total internal angle of 90 degrees, or slightly more, behind the skimmer, the optics may be readily moved in front of the array mass filter closer to the skimmer orifice in order to control the ion beam more efficiently as shown in FIG. 28. The mass filter may also be oriented to place the detectors off-axis from the neutral beam associated with the vacuum stages.

Due the low capacity (e.g., 1 liter/minute) of the roughing pump used in the exemplary embodiment, a small diameter capillary 162 is used. The small diameter capillary 162 causes viscous flow transport of the ions through the interface. In an alternative embodiment (not shown), the ions are efficiently focused from the atmospheric pressure DMS 116 to an intermediate vacuum region (e.g., a region having a pressure of 1 Torr to 10 Torr). An aspect of the challenge in transporting ions from a high pressure region to a lower pressure region through a tube or through apertures is the phenomenon that the effective ion aperture is much smaller than the actual aperture diameter. This phenomenon occurs because ions do not necessarily follow the fluid flow through the hole. Rather, the majority of the ions are de-focused at the rim at the entrance to the aperture.

The ion sampling efficiency through the skimmer 164 is determined by several factors including the capillary-skimmer spacing, the relative diameters of the capillary 162 and the skimmer 164, the electrical fields, and the pumping capacity of the high vacuum pumping system 180. As illustrated in more detail below, ions transferred to the high vacuum chamber 412 through the skimmer orifice receive "birth" energy and are accelerated to supersonic speeds. Within the QAMS 118, the ions are focused into the array of mass filters using a set of electrostatic lenses. In the illustrated embodiment, the QAMS 118 is selectively operated in three different modes. The three modes include a total ion monitoring (TIM) mode, a single ion monitoring (SIM) mode, or a continuous scan mode. In any of the three modes, the ions are detected on a Faraday plate connected to a fast response detector circuit having a response time of approximately 1 millisecond.

The exemplary embodiment of the system described herein only requires a total power budget of approximately 36 Watts. This low power budget will extend the autonomous operation of the system for a given battery capacity. The total power does not however include the power that may be used to heat the IMS 114 to about 150 degrees C. and the power that may be needed to operate the sampler module.

Figure 19:
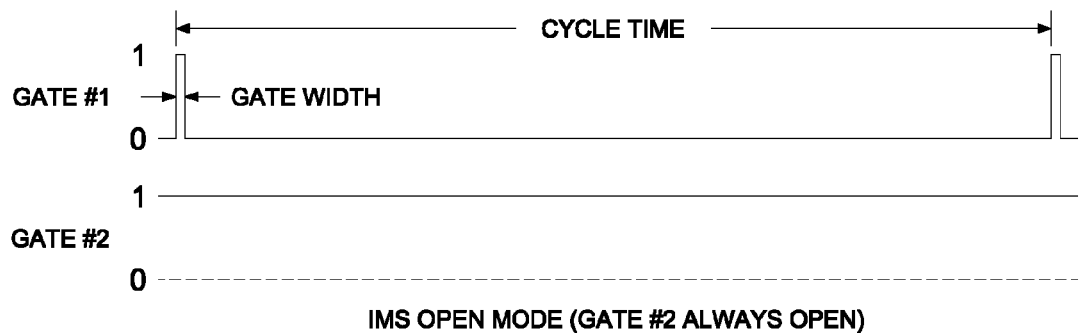
FIG. 19 illustrates a timing diagram for the first Tyndall ion gate of the IMS in the open (high sensitivity) mode with the second Tyndall ion gate of the IMS held open.
Figure 20:
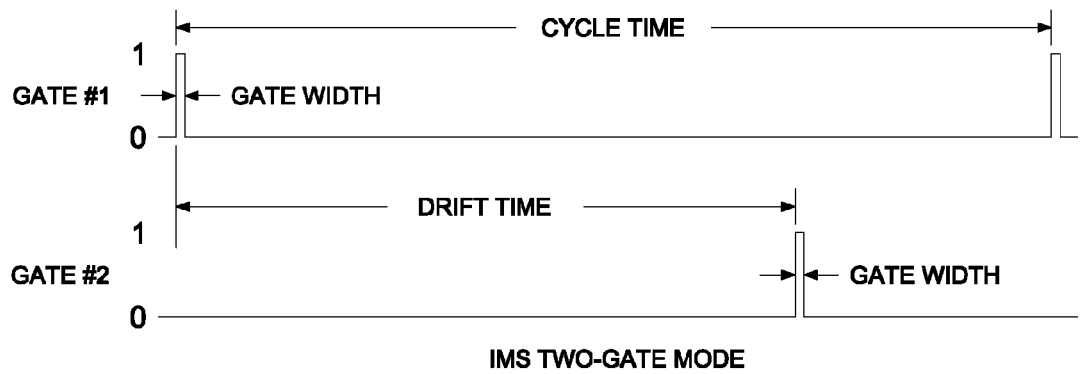
FIG. 20 illustrates timing diagrams for the first Tyndall ion gate and the second Tyndall ion gate of the IMS in the two-gate (high selectivity) mode.

As discussed above, the IMS 114 includes an inlet ion gate and an outlet ion gate that control the flow of ions into and out of the drift tube within the IMS 114. The two gates of the IMS 114 are selectively timed in two different gating modes, as illustrated in FIGS. 19 and 20. In FIG. 19, the inlet gate (gate #1) is opened for a selected duration (e.g., approximately 0.5 millisecond as shown in the illustrated timing diagram) at the beginning of each detection cycle to inject a packet of ions into the IMS cell 114 for pre-separation. The outlet gate (gate #2) remains open at all times in FIG. 19. The cycle of pulsing the inlet gate open is repeated periodically. For example, in one embodiment, the cycle is repeated approximately every 50 milliseconds. When the inlet gate is open and the outlet gate is also open, IMS spectra are generated by measuring the ion current using the open outlet gate as an in-situ Faraday detector.

The outlet gate controls the ion flow by either allowing all ions to be transferred to the next stage by leaving the outlet gate open as shown in FIG. 19, or allowing only ions in selected peaks or in a section of the mobility spectrum to be transferred to the next stage as shown in FIG. 20. In FIG. 20, the outlet gate is pulsed open at a selected time (described below) following the opening of the inlet gate. For example, in the mode illustrated in FIG. 20, the outlet gate is selectively opened for approximately 0.5 millisecond at a time selected to correspond to the travel time of the selected or targeted analyte detected by the in situ Faraday detector. The outlet gate may be opened at other times and for different durations in accordance with the types of target analytes being detected.

The low level flexibility of the IMS-DMS-QAMS approach results in different modes of operation summarized in Table 1:

TABLE 1

IMS-DMS-QAMS operating modes

| Mode | IMS | DMS | QAMS | Notes |
|---|---|---|---|---|
| 000 | 0 | 0 | 0 | Ion Source monitor |
| 001 | 0 | 0 | 1 | Mass Spec/Development |
| 010 | 0 | 1 | 0 | DMS/Development |
| 100 | 1 | 0 | 0 | IMS screening |
| 110 | 1 | 1 | 0 | IMS-DMS |
| 101 | 1 | 0 | 1 | IMS-QAMS |
| 011 | 0 | 1 | 1 | DMS-QAMS |
| 111 | 1 | 1 | 1 | IMS-DMS-QAMS |

The modes identified in Table 1 exploit trade-offs between selectivity, sensitivity, and speed. The modes are settable depending on the targeted applications. The modes are identified using the terminology (XYZ) where the value of X corresponds to the mode of the IMS, the value of Y corresponds to the mode of the DMS, and the value of Z corresponds to the mode of the QAMS. Each mode is represented by either a 0 or a 1. The digit 1 means that the device is operated in its regular mode while the digit 0 means the device is operated in a mode other than the regular mode.

In the (100) mode, the IMS is the only device turned on. In particular, the (100) mode is a mode where the IMS is operated in its regular mode using the inlet gate as an ion shutter and also using the outlet gate as a peak selector. In the (100) mode, mobility spectra are generated and are compared to spectra in a library in search of peaks corresponding to target analytes. The (100) mode is advantageously used for pre-screening, and the operation of the downstream devices is triggered upon the detection of peaks corresponding to either target analytes or interferents. A deterministic identification of molecular compounds is achieved by the DMS or the QAMS or by both the DMS and the QAMS.

In the (110) mode, the IMS-DMS provides two orthogonal detection methods operating at atmospheric pressure at high speed and low power. Operating in the IMS-DMS mode, the IMS uses the inlet gate as an ion shutter and also uses the outlet gate as a peak selector to generate ion mobility spectra of the sample analytes. The DMS is tuned to the IMS analyte by applying the compensation voltage corresponding to the analyte detected using the MS in the TIM mode or by using a separate faraday detector (not shown). The mobility spectra from the two stages are compared for orthogonal confirmation of the analyte detection. The IMS-DMS can be configured as a standalone instrument operated at atmospheric pressures without the MS stage with the addition of a Faraday detector (not shown) at the outlet of the DMS to replace the MS and associated vacuum system.

The high selectivity mode (111) is configured by pulsing out ions in a single IMS peak or a section of the IMS spectrum using the outlet gate (gate #2) with a certain width as shown in FIG. 20. In either case, the DMS is tuned to the IMS target analyte by applying the compensation voltage corresponding to the target analyte. The signal corresponding to the filtered ions is directed towards the QAMS detector operated in the total ion monitoring (TIM) mode. If the target analyte is confirmed, the QAMS is switched to the selected ion monitoring (SIM) mode and is tuned to the molecular weight of the target analyte for detection and deterministic identification. As illustrated in FIG. 19, in the single-gate mode, the width of the inlet gate (gate #1) is typically set to approximately 0.5 millisecond, and the IMS spectrum total drift time is typically approximately 50 milliseconds, which results in a duty cycle of approximately 1%. Maximum selectivity is obtained when the IMS is operated in the dual-gate mode (with the outlet gate (gate #2) selectively pulsed on), which further reduces the duty cycle depending on the width (e.g., the on time) of the outlet gate. Although the DMS is a 100% duty cycle device when operated at a constant compensation voltage, the width of the on time of the outlet gate of the IMS has little effect on the total number of ions transferred into the QAMS stage.

In the high sensitivity or pass-thru mode (011), both gates of the IMS are held open (100% duty cycle) and the DMS and QAMS are both operated in a scanning mode for target analytes from a user-established list. In the (011) mode, the IMS serves an ion-neutral separator or an ion guide.

Other modes, such as the (001) mode and the (101) mode, are useful as quality control steps during the manufacturing cycle and for instrument field troubleshooting. For example, the (001) mode serves to characterize the ion source output by operating the QAMS in either the TIM mode or the SIM mode while the (101) mode serves to characterize the IMS in dual-gate mode using the fast electrometer of the QAMS. Modes such as the (000) mode, the (110) mode, the (010) mode, and the (001) mode are used for development, troubleshooting and/or specialized applications.

In either the high selectivity (111) mode or the high sensitivity (011) mode of the IMS-DMS-QAMS system, the QAMS receives a continuous stream of ions. In the high selectivity (111) mode, the IMS pulses out only one type of ions and operates at such a high repetition rate that the IMS signal is practically detected on the same sample as the QAMS signal detected. Therefore the IMS can be approximated to a continuous ion source. In the high sensitivity (011) mode, the ions pulses exiting the DMS are pulsed out at a slow repetition rate (greater than 50 milliseconds between pulses) compared to the mass analysis. Thus, at 1 KHz, the QAMS is able to sample the DMS peaks multiple times.

Figure 21:
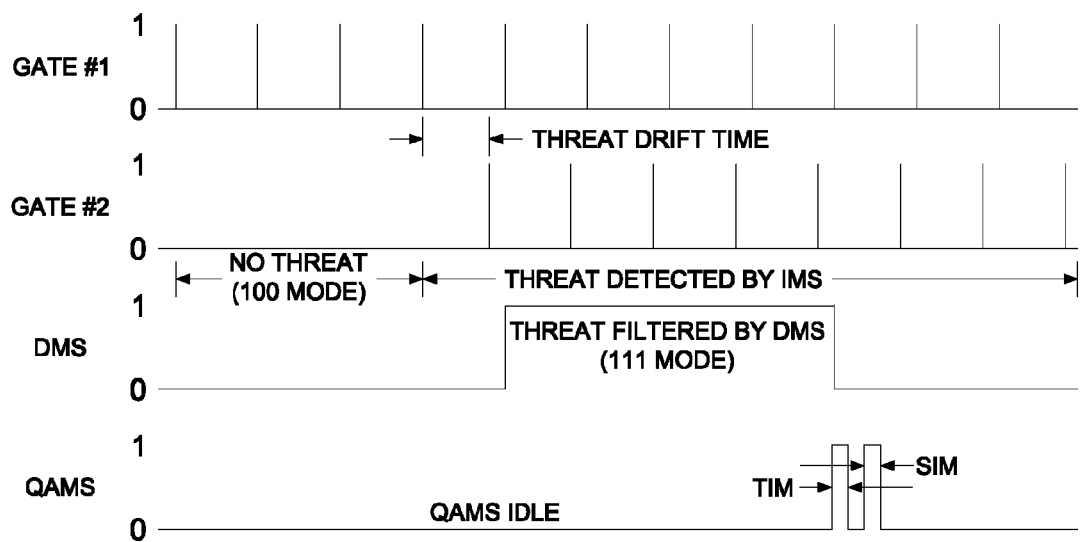
FIG. 21 illustrates timing diagrams for the IMS, the DMS and the QAMS in the high selectivity (111) mode.

FIG. 21 illustrates timing sequences of the operation of the three instruments in the high sensitivity (100) mode prior to the detection of a target analyte followed by the operation of the three instruments in the high selectivity (111) mode after the target analyte is initially detected. The timing diagrams for the inlet gate (gate #1) and the outlet gate (gate #2) in the IMS 114 correspond to the diagrams in FIGS. 19 and 20 except that that the time scale is compressed. The DMS timing diagram is low when the DMS 116 is not active and is high when the DMS 116 is active. The QAMS timing diagram is low when the QAMS 118 is in the idle mode. The system controller 120 (FIG. 1) switches the instruments over to the high selectivity or "full load" (111) mode to verify the identity of the target compound, and all three modes of ion separation are employed in the (111) mode. The IMS 114 performs pre-screening duties by acquiring full chromatogram spectra using its in-situ Faraday detector (described below). Discrete pulses of ions are injected into the drift tube within the IMS 114 by activating the inlet gate (gate #1) every 30 milliseconds for about 0.2 millisecond as shown in the left portion of FIG. 21 for a condition where no target analyte is detected. The system controller 120 receives the output of the in situ Faraday detector and accesses a stored table of drift times to determine whether any of the peaks of the spectra correspond to a potential target analyte.

When a potential target analyte peak is detected, the system controller 120 activates the outlet gate (gate #2) at precisely the time the target analyte peak lies in the IMS spectrum as illustrated in FIG. 21. The time for opening the outlet gate is selected by the microcontroller to ensure that only ions accounting for the "suspect" peak or peaks are injected into the DMS 116. When the outlet gate is activated, the DMS 116 is tuned to the particular target analyte. By applying the appropriate compensation voltage, which is obtained from a look-up table within the microcontroller, target analyte ions are filtered within the cell and are continuously carried by a flow of gas at atmospheric pressure toward the exit of the DMS 116. The ions are moved pneumatically inside the DMS 116, which results in residence times of at least 50 milliseconds, depending on the dimensions of the cell of the DMS 116 at typical gas flows. The ions are transported through the capillary-skimmer vacuum interface 160, are focused into the QAMS 118, and are detected using a 1-millisecond response time Faraday detector in the QAMS 118. After 50 milliseconds, the system microcontroller activates the QAMS 118 in the TIM mode to confirm the presence of a pulse of gas and thus serves as the detector for the DMS 116. If a confirmation of the gas is obtained, the QAMS 118 is tuned to the molecular weights of interest (molecular parent and/or daughter ions) by applying the proper RF voltage and the proper DC voltage to operate in SIM mode. The detection and identification of potential target analytes are based on the measurement of a signal at a given molecular weight for a given signal-to-noise ratio. In the case of multiple potential target analyte peaks appearing in the IMS spectrum, ions corresponding to each target analyte are pulsed out of the IMS 114 sequentially and are processed according to pre-determined criteria such as relative amplitude. Elaborate analysis can also be performed in this mode by using the QAMS 118 as the detector for both the IMS 114 and the DMS 116. In particular, three-dimensional response surfaces for the analyte of interest are produced by scanning across both the IMS peak (using the outlet gate) and the DMS peak (using the CV) data. By scanning the time at which the outlet gate is activated (open) and maintaining constant the optimum value of the CV corresponding to the target analyte, both the mobility and the differential mobility of the peak of the target analyte are generated on a three-dimensional surface.

In the high sensitivity (011) mode, the IMS 114 serves as an ion guide while the DMS 116 and the QAMS 118 provide continuous ion discrimination and detection by operating in jump scan mode searching for target analytes from a user-established list. As the DMS 116 scans through different compensation voltages, the QAMS 118 acts as the detector for the DMS 116 by operating in the TIM mode as indicated by the first pulse in the QAMS diagram of FIG. 21. When a signal is detected, the QAMS 118 is switched to the SIM mode to detect a signal at the mass of the molecular parent as indicated by the second pulse in the QAMS diagram of FIG. 21. Tuning to the molecular weight of daughter ions is easily performed if additional confirmation is required.

The data presented herein is from corresponding "full sized" bench top instruments show proof of concept that the disclosed integration is possible and is useful for analytical purposes. In the proof-of-concept system, ions are generated by an electrospray ionization source. A dome type DMS (or FAIMS) cell is mounted to the heated capillary of a Thermo Finnigan LCQ Deca quadrupole ion trap mass spectrometer. The exit of the IMS cell is maintained between 600 volts and 1,000 volts greater than the curtain plate voltage to establish an electric field gradient from the IMS to the DMS cells. The ions from the sample are introduced into the IMS cell at a flow rate of 1-3 microliters/minute. The DMS carrier gas is a nitrogen (60%) and helium (40%) mixture at a flow rate of 2 liters/minute.

Figure 22:
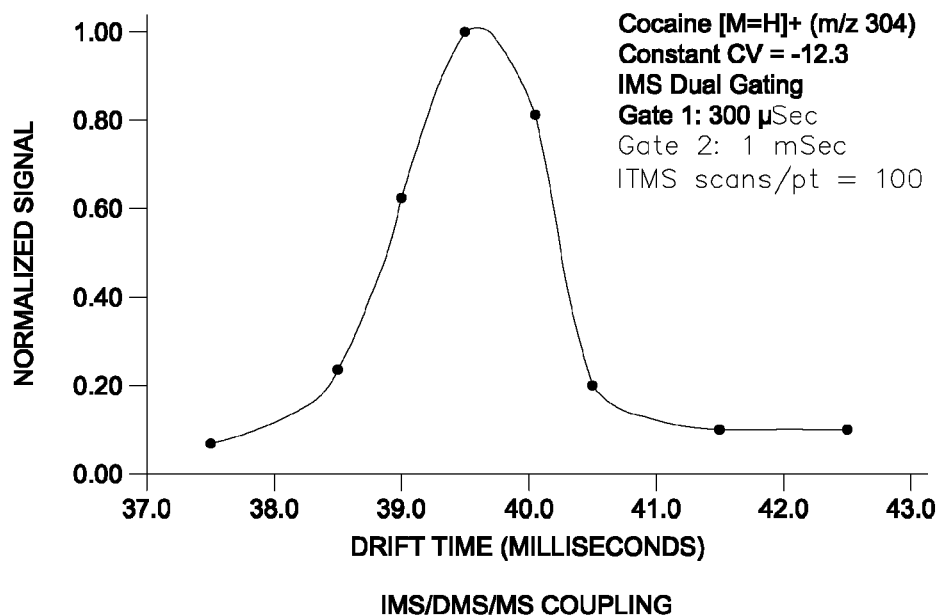
FIG. 22 illustrates an ion mobility spectrum acquired at a constant compensation voltage (CV) of −11.1 volts for cocaine having a mass-to-charge ratio (m/z) of 304.
Figure 23:
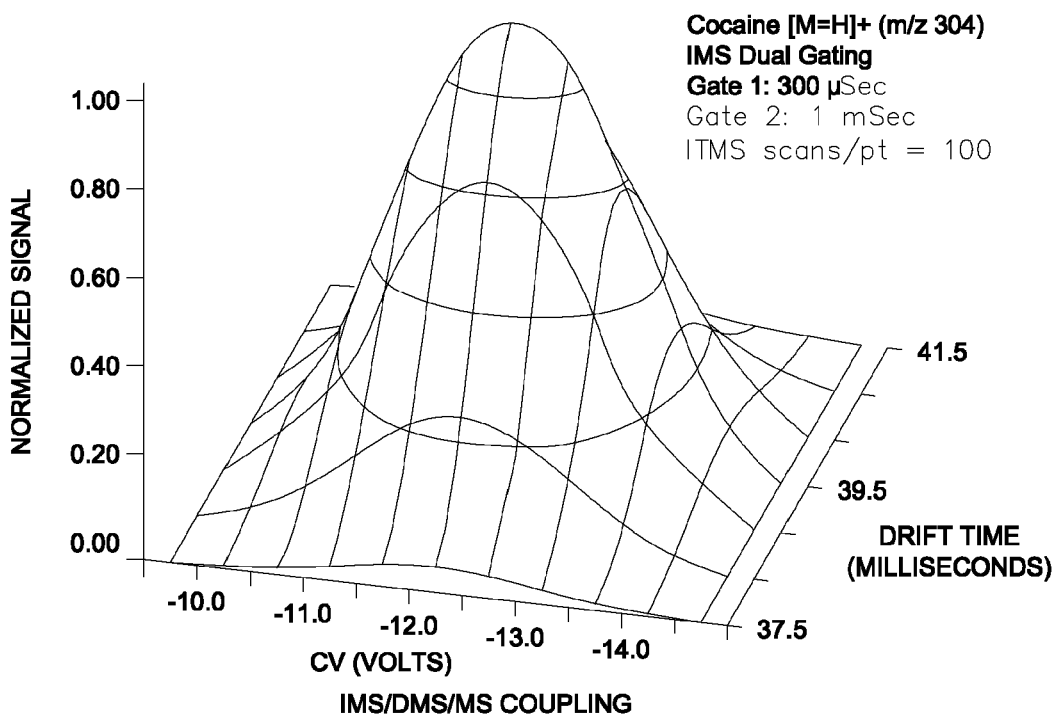
FIG. 23 illustrates a three-dimensional response surface for an analyte of interest.

FIG. 22 illustrates the results of an experiment where the optimum compensation voltage for protonated cocaine ion (mass-to-charge ratio (m/z)=304) transmission is determined and set constant while the IMS was operated in the dual gate mode described above. To obtain a desired duty cycle and an efficient ion transmission, the inlet gate (gate #1) is opened for 0.5 millisecond and the outlet gate is opened for 1 millisecond at an arrival time based on data obtained from the literature. Data is obtained by performing 100 analytical scans with the outlet gate open to allow only the ions which have an arrival time in the 5-millisecond interval between 37.5 milliseconds and 42.5 milliseconds to pass the ions to the FAIMS device. To obtain the ion mobility peak profile, the arrival time is incremented by 0.5-millisecond steps between 37.5 milliseconds and 42.5 milliseconds. This process is repeated in order to obtain a reasonable signal-to-noise ratio. The combination of the IMS peak data and the DMS peak data is used with the mass spectrum to produce a three-dimensional response surface for the analyte of interest, which is illustrated in FIG. 23. In FIG. 23, the three-dimensional spectrum is produced by varying both the compensation voltage (CV) and the arrival time with the mass spectrometer (MS) set at a mass-to-charge ratio of 304 (i.e., m/z=304).

Figure 24:
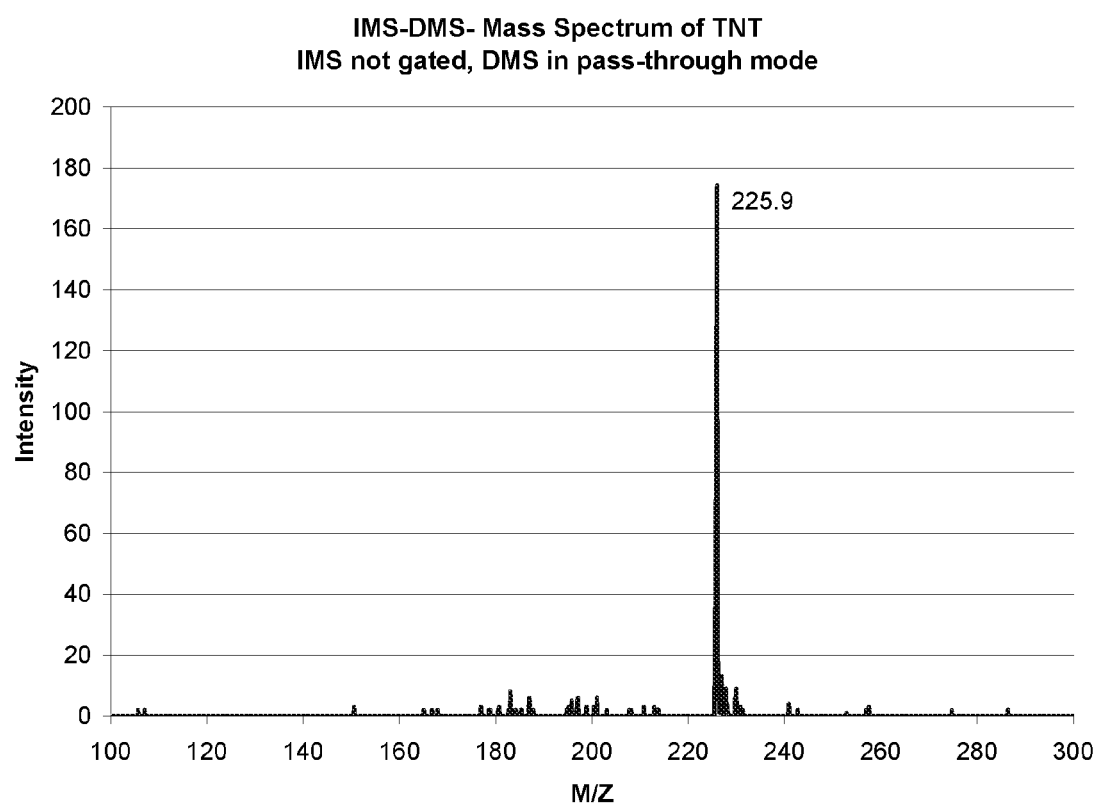
FIGS. 24 and 25 illustrate comparisons of mass spectra obtained in the open IMS (high sensitivity) mode (FIG. 24) versus the two-gate IMS mode (FIG. 25).
Figure 25:
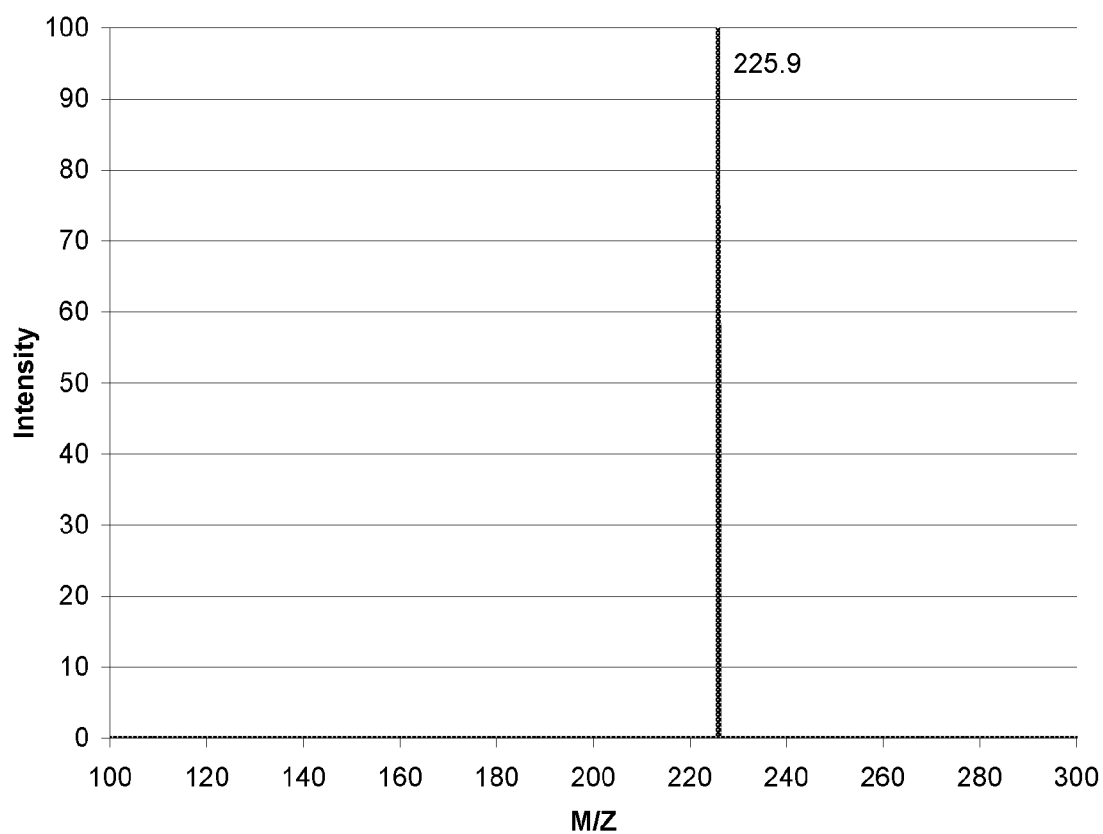
Figure 26:
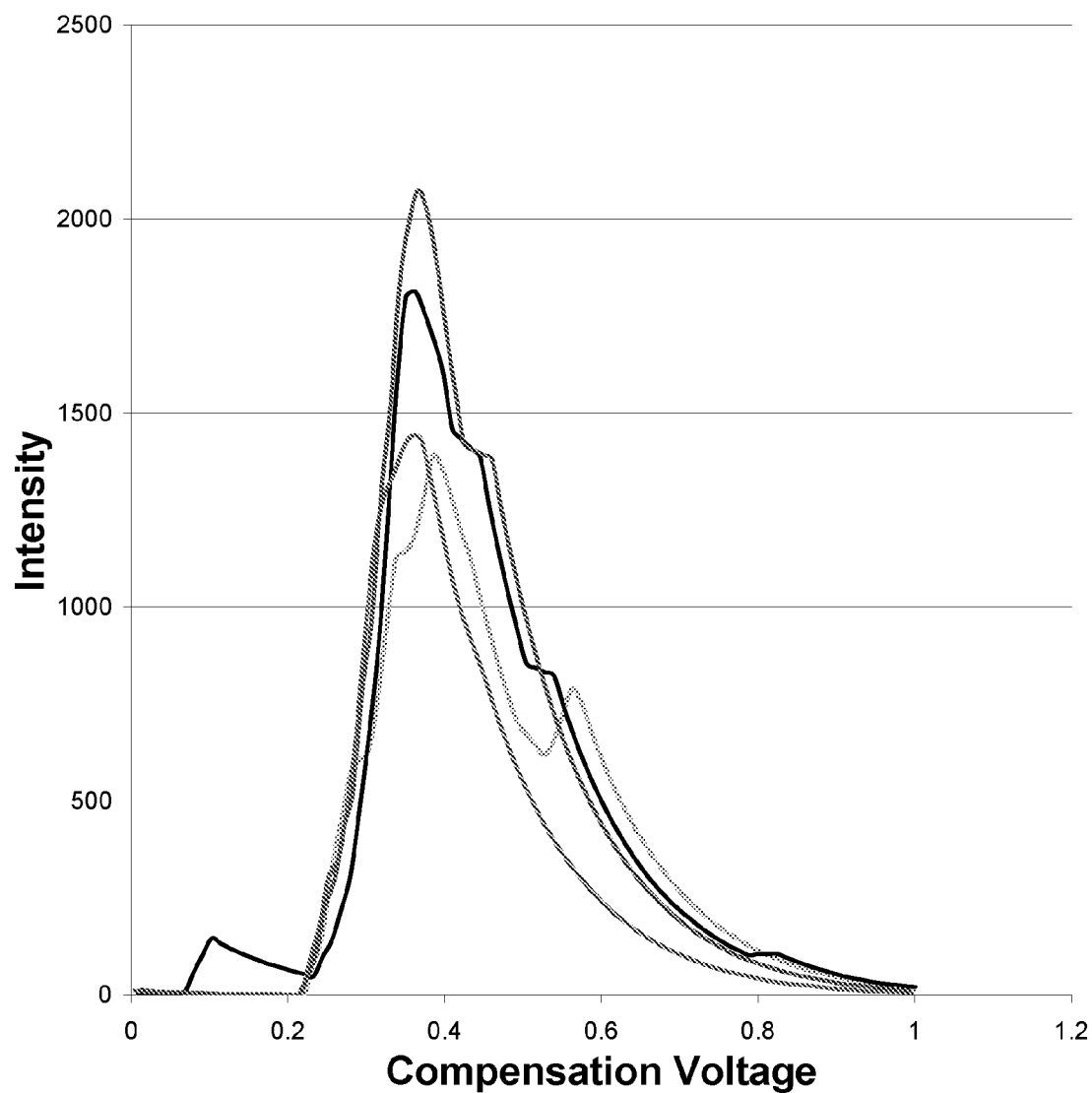
FIGS. 26 and 27 illustrate comparisons of compensation voltage spectra obtained in the open IMS (high sensitivity) mode (FIG. 26) versus the two-gate IMS mode (FIG. 27)
Figure 27:
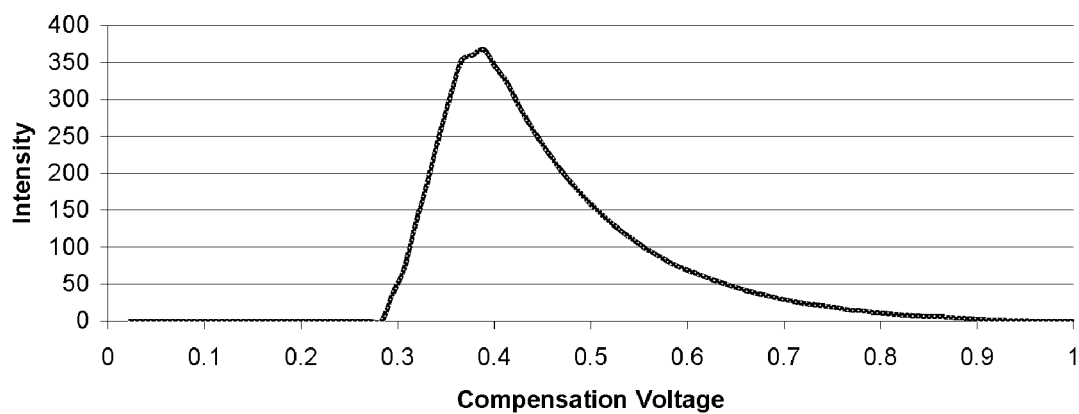

FIGS. 24 and 25 illustrate comparisons of mass spectra obtained in the open IMS (high sensitivity) mode (FIG. 24) versus the two-gate IMS mode (FIG. 25). FIGS. 26 and 27 illustrate comparisons of compensation voltage spectra obtained in the open IMS (high sensitivity) mode (FIG. 26) versus the two-gate IMS mode (FIG. 27). As shown in FIGS. 25 and 27, the resolution and the signal-to-noise ratio are both clearly improved when the IMS is in the dual-gate mode. FIG. 28 illustrates a well-resolved, higher signal-to-noise ratio mass spectrum obtained by introducing 5 parts per million of TNT in the high selectivity mode.

Figure 29:
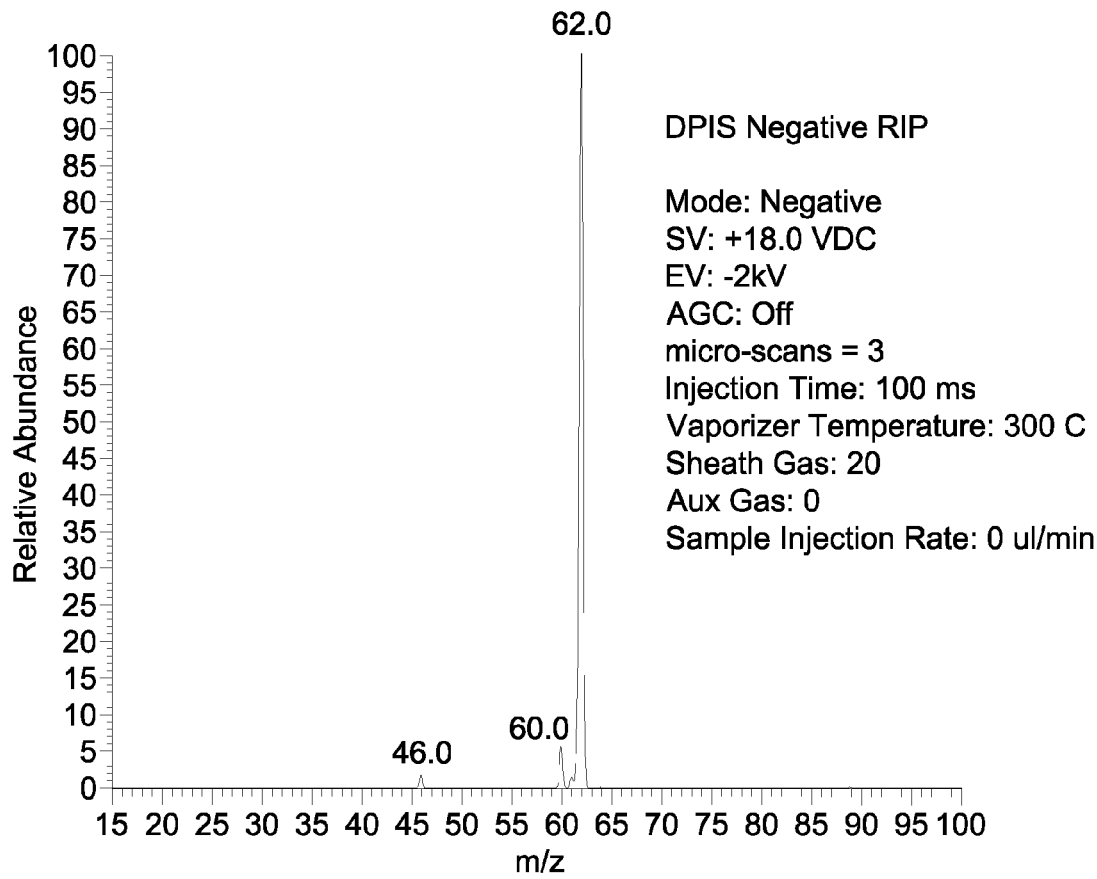
FIG. 29 illustrates the reagent ion peak obtained with a liquid chromatography quadrupole (LCQ) ion trap mass spectrometer in a negative mode.
Figure 30:
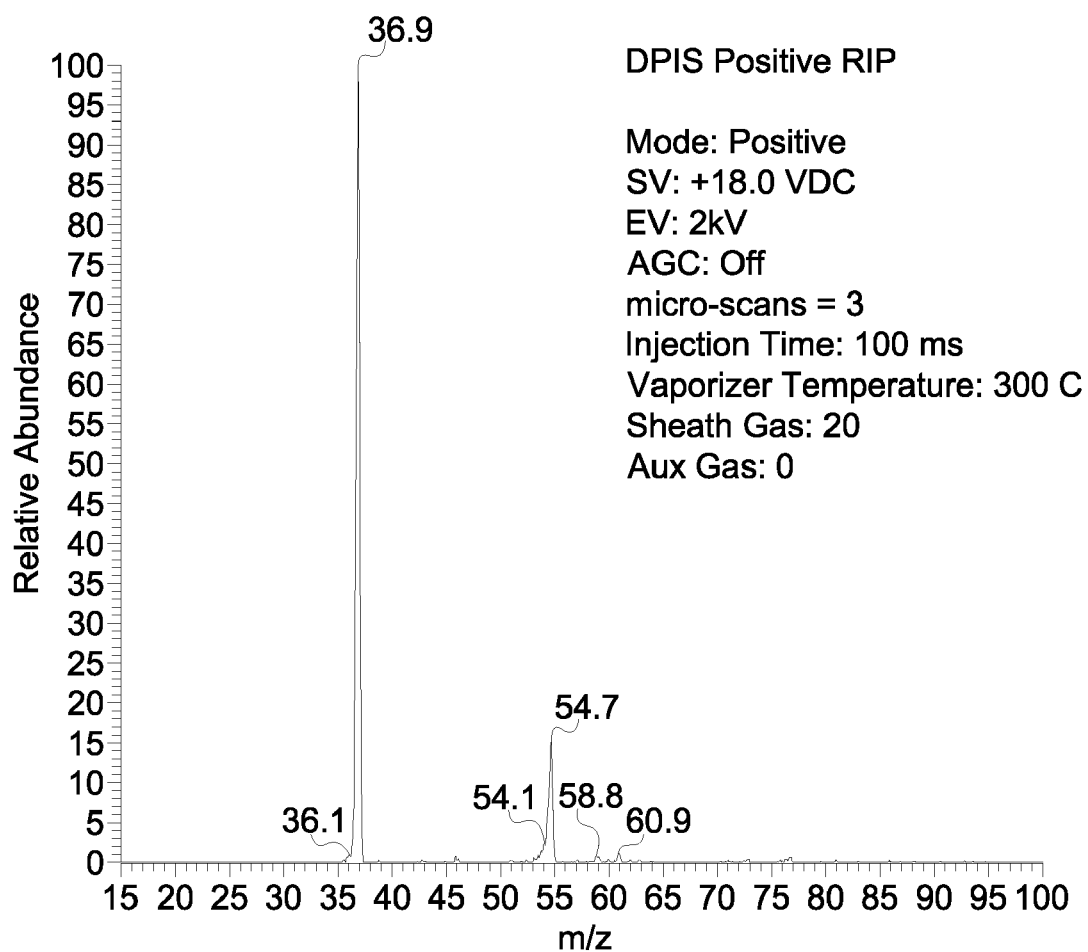
FIG. 30 illustrates the reagent ion peak obtained with a liquid chromatography quadrupole (LCQ) ion trap mass spectrometer in a positive mode.
Figure 31:
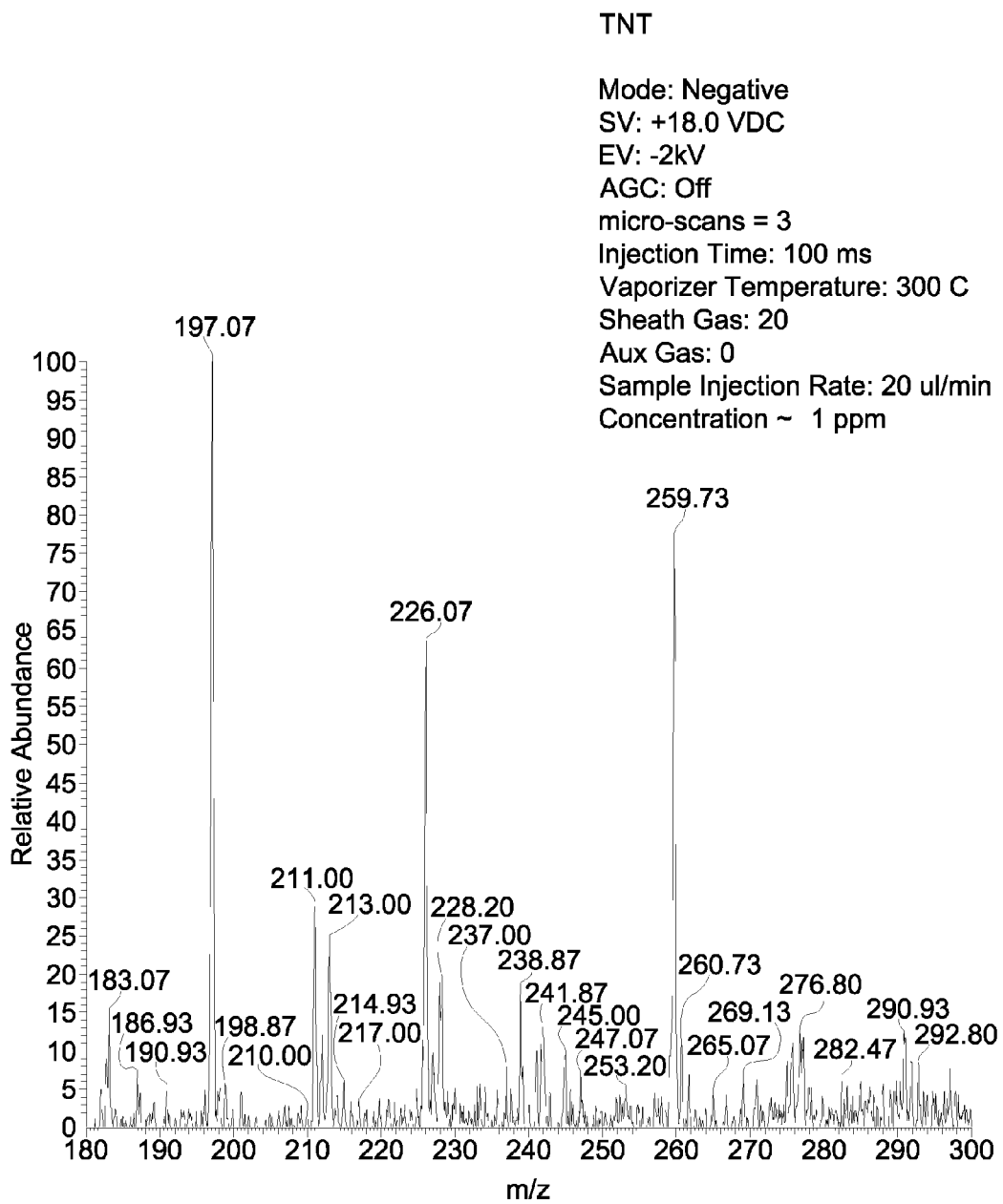
FIG. 31 illustrates the TNT spectrum obtained using the DPIS of FIG. 3.

FIGS. 29 and 30 illustrate the reagent ion peaks obtained with an liquid chromatography quadrupole (LCQ) ion trap mass spectrometer in a negative mode and a positive mode respectively. The reagent ion peaks (RIP) match peaks that have been documented previously in the literature. The $NO_3^-$ ion created with the ion source of FIG. 3 is shown to cluster well with explosives molecules such as RDX, PETN, TNT and NG. For example, FIG. 31 illustrates the TNT spectrum obtained using the DPIS of FIG. 11.

Figure 32:
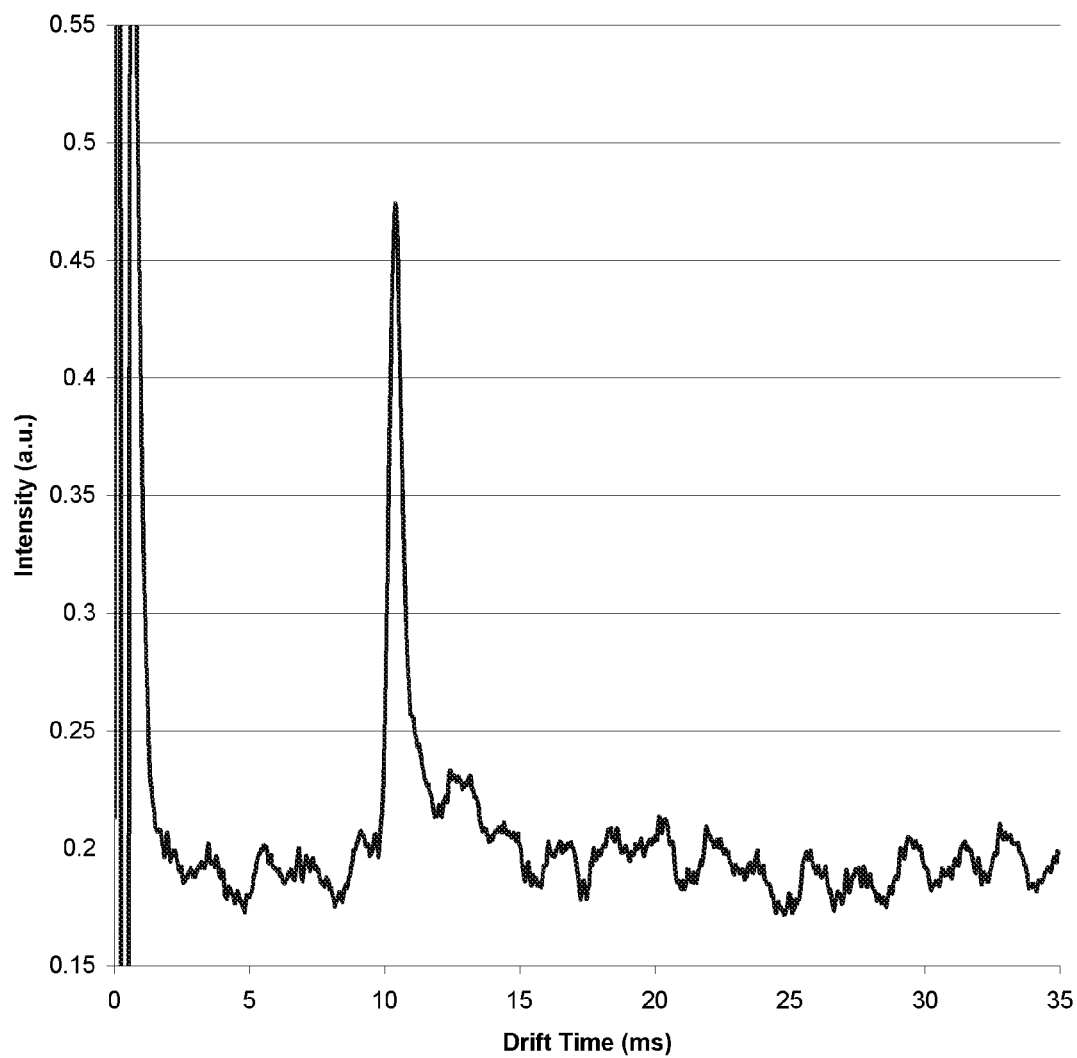
FIG. 32 illustrates the spectra of a typical ion mobility test-standard, 2,4-lutidine, when the DPIS ionizer is set in the positive mode and the in-situ IMS Faraday plate is used as the detector to acquire the spectra.

FIG. 32 illustrates the spectra of a typical ion mobility test-standard, 2,4-lutidine, when the DPIS ionizer is set in the positive mode and the in-situ IMS Faraday plate is used as the detector to acquire the spectra. The IMS and test compounds conditions are presented in Table 2.

TABLE 2

The parameters of the ion mobility device and the mobility values of a test compound

| | |
|---|---|
| Drift Length | 64.0 millimeters |
| Temperature of Drift Region | 394 degrees Kelvin |
| Atmospheric Pressure | 694.7 mmHg |
| Electric Field | 281.72 volts/centimeter |
| Drift Gas | Compressed Air |
| Gate Open Time | 200 microseconds |
| $K_o$ (mobility) 2,4-lutidine dimer | 1.45 $cm^2$/volt-second |

A conventional commercial bench top analytical equipment is modified to generate a suitable waveform for DMS separation. For example, an Ionalytics Alpha prototype waveform generator with additional capacitance loading generates a suitable waveform to drive the miniature DMS 116. The waveform is applied to one of the plates and a reference lead is connected to the other plate. Each individual component of the waveform is capacitance tuned for the electrode, and the components are added together to produce a waveform similar to the one shown in FIG. 33. A suitable waveform comprises the sum of two sinusoidal components with one component having a frequency that is twice the frequency of the other component and having a phase shift relative to the other component. For example, an exemplary waveform may be generated in accordance with the following equation:

$$V_a(t) = CV + fDV \sin(\omega t) + (1-f)DV \sin(2\omega t - \phi)$$

where:
$V_a(t)$ is the total voltage applied to the electrode;
CV is the compensation voltage, which comprises a variable DC offset (−200 volts to +200 volts);
DV is the dispersion voltage (−1000 volts to +1000 volts);
$\phi$ is a phase shift for the second waveform component of 90 degrees;
f is a weighting factor (0.67 for the ideal case); and
$\omega$ is the radian frequency, which is 27 times the frequency of the primary waveform component in a range of 1 MHz to 2 MHz.

Figure 33:
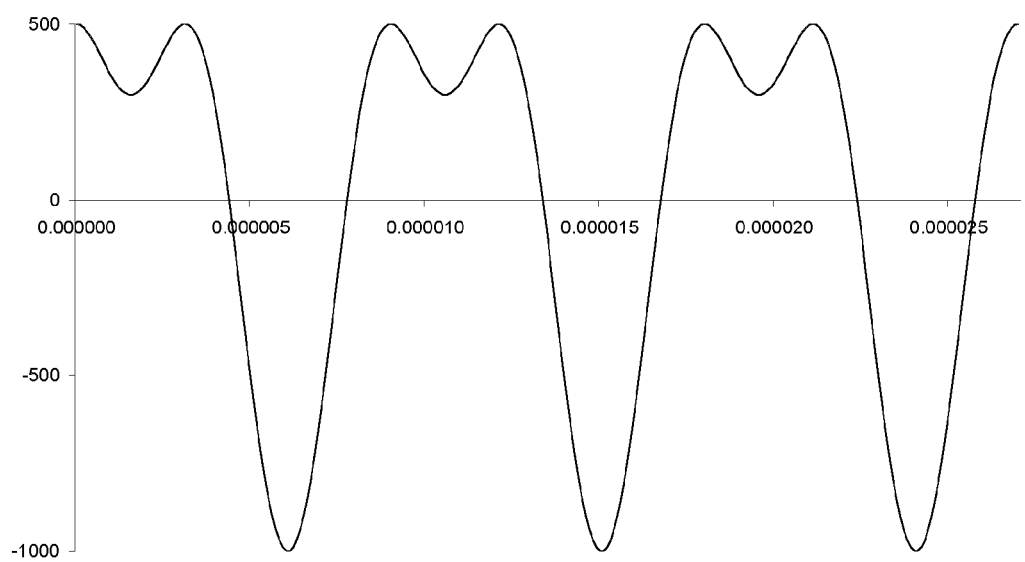
FIG. 33 illustrates a waveform applied to an electrode plate of the DMS cell of FIG. 20 when a reference lead is connected to the other electrode plate, wherein the waveform comprises the sum of individual component waveforms that are capacitance-tuned for the electrode plate.

In FIG. 33, the dispersion voltage is only 1,000 volts from 0 volts to the negative peak corresponding to a factor of 4 lower than the voltage required for full-size DMS cells with analytical gaps of 2 millimeters; however, the analytical gap is smaller by a factor of 4. The net field needed for separation of ions within the DMS 116 is identical for bench top operation on commercially available systems.

After tuning the waveform to the DMS capacitance (1.33 picofarads), the DMS 116 is mounted in the source of a LCQ quadrupole ion trap mass spectrometer. An electrospray ionization (ESI) source generates ions from a solution containing a mixture of three small drug compounds. No carrier gas is used and no attempt to made to perform additional ion desolvation. The DC compensation voltage is varied from 0 volt to −20 volts during a span of 2 minutes, and a compensation voltage (CV) spectrum is obtained. The CV spectrum shows ion separation for the three compounds. The CV peaks are broad and unsuitable for analytical use; however, the broad peaks are attributable to the lack of carrier gas and to the lack of ion desolvation in the source.

The basic configuration of the system disclosed herein is an IMS, which is coupled serially to a DMS cell, which is coupled serially to a QAMS. Efficient transfer of the ions from the IMS to the DMS is accomplished through a pneumatic or electrostatic funnel. The system includes an atmospheric pressure mass spectrometer interface that facilitates the efficient transport of ions at the exit of the DMS to the QAMS operating at 1 milliTorr. The DMS-QAMS vacuum interface comprises the combination of a small diameter capillary and a skimmer. The pressure between the exit of the capillary and the skimmer is about 1 Torr and is established by the miniature pump discussed above.

A major advantage of the IMS-DMS-QAMS approach is the universal detection of known and improvised explosives. Ion mobility and mass spectrometry are proven techniques that are capable of detecting and specifically identifying the full range of explosive compounds, including military, commercial, improvised, and home made explosives as well as correlated precursor, binders, stabilizers, and any taggant chemicals that are used to make an IED. While conventional explosives detectors, such as the ones currently deployed in airports, rely on the presence of particular molecular radicals in order to form detectable ions, mass spectrometry based instruments do not and can therefore detect a wider range of threats including peroxide and liquid explosives.

Another major advantage of the IMS-DMS-QAMS approach is the high probability of detection. The non-radioactive ion source (Distributed Plasma Ion Source) uses an atmospheric pressure chemical ionization process that minimizes molecular fragmentation and is compatible with both positive and negative ionization of explosives molecules. The novel IMS-DMS-QAMS analysis technique provides up to three different orthogonal detection vectors to maximize the probability of detection and to minimize false alarms.

Another major advantage of the IMS-DMS-QAMS approach is the flexibility of the system. The small size of the system enables the system to be adapted to different packaging footprints and to a variety of user interfaces. Armed with a remote sample collection device, the IMS-DMS-QAMS system can be incorporated into new or existing X-ray scanners and walk-through portals and can share the same user interface. This feature leads to increased security per check point without the need for additional operators. The system has built-in high sensitivity and high selectivity modes that enable the user to switch from rapid screening to confirmation analysis. In non-real-time applications, higher sensitivity IMS-DMS-QAMS systems having built-in fast pre-concentration devices such as MEMS miniature thermal desorbers are able to tackle scenarios where, due the extremely low vapor pressures of some explosives, efficiency of sample acquisition is uncertain. Other modes include forensics investigations analysis whereby the device scans for unknown substances at crime scenes. Other options include a low-cost stand-alone explosives "trigger" detector where the IMS-DMS modules alone may serve as an atmospheric pressure replacement for the MS.

Another major advantage of the IMS-DMS-QAMS approach is the ability of the system to operate in real-time. For real-time detection, the instrument is programmed to automatically sample, concentrate, and process aerosol and surface samples for continuous measurement, confirmation, and analysis of explosives and corollary compounds all in 1-5 seconds from sample introduction. By coupling the automated sampling and IMS technology, the system rapidly acquires and separates the target explosive vapors from background chemicals in near real time, thereby replacing the time consuming steps of concentration, gas chromatography or both needed in typical GC-MS based detection systems. During the rapid sampling and analysis cycle (1-5 seconds), the alarms are sounded (if the user desires); specific data is displayed for the operator; and the data is wirelessly transmitted to a control unit or monitoring center in a larger network of sensors. The programmable cycle time accommodates different sampling, analyzer, and detector scanning modes to optimize the sniffer for speed, sensitivity, specificity, and the number of target compounds. Fast (sub-second) calibration protocols are performed automatically and continuously in order not to interfere with the operation. An indicator flashes during the calibration. In the case of a hit, a "degas" protocol is activated in order to speed up the clear down process.

Another major advantage of the IMS-DMS-QAMS approach is the portability of the system. The IMS-DMS-QAMS systems are designed as "hand-held" portable instruments estimated to weigh in at about 7 lbs (without the battery) and to draw a maximum of 70 Watts in a small and rugged 4-inch×4-inch×12-inch enclosure or 8-inch×8-inch× 3-inch enclosure. The on-board microcomputer and wireless networking capability supports remote control and operation as part of a sensor network. The small size and low power also provides the flexibility to be easily concealed, so the system can be unobtrusively carried for clandestine searches or hidden at fixed or temporary checkpoints.

Another major advantage of the IMS-DMS-QAMS approach is the safe and easy operation of the system. The IMS-DMS-QAMS system is inherently safe for the operators and public as compared to stand-off detectors that must employ ionizing dangerous radiation, x-rays, neutrons, microwaves, or laser energy. While most IMS devices are mainly based on the ionization by radioactive sources as $^{63}$Ni, $^{241}$Am and $^{3}$H, the system disclosed herein employs harmless corona discharge which avoids radiation licensing, safety, and disposal problems. Surface and aerosol sampling are performed automatically and by wireless remote control allowing the operator to remain at a safe distance away from the suspected explosives package or checkpoint. The system is small enough that the system can easily be deployed on a small remote controlled ground vehicle as inexpensive as a radio controlled model truck to keep the operators at a safe distance from any suspected IEDs. Full integration helps the robot make independent decisions to enhance the robot's autonomy during military reconnaissance operations.

Another major advantage of the IMS-DMS-QAMS approach is the affordability of the system. The price of the DPIS-IMS-DMS-QAMS configuration of the IMS-DMS-QAMS system is estimated to be $7,500 per unit with high volume production and sales. This production cost estimate is substantiated by the current commercial price of a QAMS system, including RF and control electronics, which is currently approximately $4,800 at production rates of 1000 units. MEMS fabrication of the IMS and DMS cells, the miniature vacuum pump, the supporting electronics and the PDA computer with broadband wireless capability is estimated to add $2,700 to the price of each unit in production volumes. Using disposable components, the IMS-DMS-QAMS explosives detector is designed to operate over long periods with minimal life cycle operating and maintenance cost.

The present invention is disclosed herein in terms of a preferred embodiment thereof, which provides a real-time chemical detection system as defined in the appended claims. Various changes, modifications, and alterations in the teachings of the present invention may be contemplated by those skilled in the art without departing from the intended spirit and scope of the appended claims. It is intended that the present invention encompass such changes and modifications.

We claim:

1. A system for analyzing materials at or near atmospheric pressure, comprising:
   a sampling inlet that receives a input sample to be analyzed;
   an ion source to ionize the input sample to produce an ionized sample;
   a drift tube ion mobility spectrometer (IMS) stage having an IMS inlet that receives the ionized sample and having an IMS outlet, the IMS stage having a time-independent electrical field that is applied to the ionized sample to move the ionized sample toward the IMS outlet, the IMS stage identifying the ionized sample based on time of arrival at the IMS outlet;
   a high-field asymmetric-waveform ion mobility spectrometer (FAIMS) operating as a differential mobility spectrometer (DMS) stage coupled in series with the IMS stage to receive the ionized sample from the IMS stage;
   a fast Faraday detector to analyze the ionized sample exiting the DMS stage; and
   a sample vacuum pump to cause the ionized sample to flow through the system,
   wherein the IMS stage comprises an ion mobility drift cell having a first ion gate and a second ion gate, the system further comprising a system controller that controls the release, the acceleration, and the timing of packets of ions produced in the ion source by controlling the first ion gate and the second ion gate of the ion mobility drift cell, the system controller selectively operating the first ion gate and the second ion gate in a first mode of operation and a second mode of operation, wherein:
   in the first mode of operation:
      the system controller opens the first ion gate for a selected duration at the beginning of each detection cycle to inject a packet of ions into the IMS for pre-separation;
      the system controller opens the second ion gate throughout the detection cycle; and
      the IMS stage producing an IMS spectrum by measuring the ion current in a Faraday detector in the IMS stage while the second ion gate remains open; and
   in the second mode of operation:
      the system controller opens the first ion gate for a selected duration at the beginning of each detection cycle to inject a packet of ions into the IMS stage; and
      the system controller pulses the second ion gate open at a selected time after opening the first ion gate to control the ion flow by allowing only ions in selected peaks or in a section of the mobility spectrum to be transferred to the DMS stage in accordance with the travel time of the preselected analyte to be detected by the Faraday detector.

2. The system as defined in claim 1, wherein:
   sample molecules, vapors, and particulates carried or suspended in a gas or air are drawn through an orifice and into the sampling inlet by a fan or a vacuum pump;
   any surface contacting the sample air flow is heated or comprises an inert material that does not condense, stick or react with the sample, or is heated and comprises an inert material;
   the sampling inlet is connectable to other devices to collect, concentrate, or extract sample particulates from surfaces, liquid, or other matrices and to prepare the sampled materials for introduction into the sampling inlet in gaseous form; and
   the sample molecules, vapors, and particulates are carried in the air flow and transported to the ion source.

3. The system as defined in claim 1, wherein:
   the sample ions are ionized by passing through one of a positive or negative distributed plasma generated by a non-radioactive ion source operated at or near atmospheric pressure; and
   the ion source is automatically switchable between a positive ionization mode and a negative ionization mode.

4. The system as defined in claim 1, wherein the IMS stage comprises:
   an ion mobility drift cell comprising a series of spaced-apart electrical conductor rings and mounted on a circuit board and electrically connected to a source of an electrical field, the ion mobility drift cell having an entrance and an exit;
   a first ion gate mounted on the circuit board and positioned in series with the electrical conductor rings of the ion mobility drift cell at or near the entrance of the ion mobility drift cell;
   a second ion gate mounted on the circuit board and positioned in series with the electrical conductor rings of the ion mobility drift cell at or near the exit of the ion mobility drift cell; and
   a faraday detector mounted on the circuit board and positioned at the exit of the ion mobility drift cell.

5. The system as defined in claim 1, wherein the DMS is configured to:
   excite the analyte ions in high frequency, high amplitude electric fields;
   filter the ions by applying a compensation voltage (CV) selected to allow only ions of the corresponding ion mobility to pass through the DMS cell; and
   pneumatically move the ions through and out of the DMS via a gas flow established in the DMS to an ion detector.

6. The system as defined in claim 5, wherein the DMS stage provides the ions to a separate ion detector to thereby enable the IMS stage and the DMS stage to operate in a stand-alone IMS-DMS instrument configuration.

7. The system as defined in claim 1, wherein:
   a mass spectrometer (MS) stage is coupled in series with the DMS stage to receive the ionized sample after the ionized sample passes through the DMS stage;
   the IMS stage comprises an inlet gate that operates as an ion shutter and comprises an outlet gate operable as an ion shutter and also operable as a peak detector, the IMS stage being controllable independently of the DMS stage and the MS stage to selectably operate in a high sensitivity mode with the outlet gate operating as the peak detector and to selectably operate in a high selectivity mode with the outlet gate operating as the ion shutter to only pass ions that arrive at the outlet gate at a selectable time after the inlet gate opens; and the operating characteristics of the DMS stage are controllable independently of the IMS stage and the MS stage.

8. A combination ion mobility spectrometer (IMS), differential mobility spectrometer (DMS) and mass spectrometer (MS) operated in series in at least two stages, comprising:

a sampling inlet that receives a input sample to be analyzed;

an ion source to ionize the input sample to produce an ionized sample;

a drift tube ion mobility spectrometer (IMS) stage having an IMS inlet that receives the ionized sample and having an IMS outlet, the IMS stage having a time-independent electrical field that is applied to the ionized sample to move the ionized sample toward the IMS outlet, the IMS stage identifying the ionized sample based on time of arrival at the IMS outlet;

a high-field asymmetric-waveform ion mobility spectrometer (FAIMS) operating as a differential mobility spectrometer (DMS) stage coupled in series with the IMS stage to receive the ionized sample from the IMS stage;

a mass spectrometer (MS) stage coupled in series with the DMS stage to receive the ionized sample after the ionized sample passes through the DMS stage;

a roughing vacuum pump to evacuate a first stage of the MS stage to a first pressure below atmospheric pressure; and a high vacuum pump to evacuate a second stage of the MS stage to a second pressure below the first pressure, wherein the IMS stage comprises an ion mobility drift cell having a first ion gate and a second ion gate, and wherein the combination further comprises a system controller that controls the release, the acceleration, and the timing of packets of ions produced in the ion source by controlling the first ion gate and the second ion gate of the ion mobility drift cell, the system controller selectively operating the first ion gate and the second ion gate in a first mode of operation and a second mode of operation, wherein:

in the first mode of operation:

the system controller opens the first ion gate for a selected duration at the beginning of each detection cycle to inject a packet of ions into the IMS stage for pre-separation;

the system controller opens the second ion gate throughout the detection cycle; and the IMS stage producing an IMS spectrum by measuring the ion current in a Faraday detector in the IMS stage while the second ion gate remains open;

and in the second mode of operation:

the system controller opens the first ion gate for a selected duration at the beginning of each detection cycle to inject a packet of ions into the IMS stage; and the system controller pulses the second ion gate open at a selected time after opening the first ion gate to control the ion flow by allowing only ions in selected peaks or in a section of the mobility spectrum to be transferred to the DMS stage in accordance with the travel time of the preselected analyte to be detected by the Faraday detector.

9. The combination as defined in claim 8, wherein:

sample molecules, vapors, and particulates carried or suspended in a gas or air are drawn through an orifice and into the sampling inlet by a fan or a vacuum pump;

any surface contacting the sample air flow is heated or comprises an inert material that does not condense, stick or react with the sample, or is heated and comprises an inert material;

the sampling inlet is connectable to other devices to collect, concentrate, or extract sample particulates from surfaces, liquid, or other matrices and to prepare the sampled materials for introduction into the sampling inlet in gaseous form; and the sample molecules, vapors, and particulates are carried in the air flow and transported to the ion source.

10. The combination as defined in claim 8, wherein:

the sample ions are ionized by passing through one of a positive or negative distributed plasma generated by a non-radioactive ion source operated at or near atmospheric pressure; and the ion source is automatically switchable between a positive ionization mode and a negative ionization mode.

11. The combination as defined in claim 8, wherein the DMS stage is configured to:

excite the analyte ions in high frequency, high amplitude electric fields;

filter the ions by applying a compensation voltage (CV) selected to allow only ions of the corresponding ion mobility to pass through the DMS stage; and pneumatically move the ions through and out of the DMS stage via a gas flow established in the DMS stage to an ion detector.

12. The combination as defined in claim 11, wherein the DMS stage provides the ions to the MS stage.

13. The combination as defined in claim 8, wherein the MS stage includes a set of electrostatic lenses to focus ions into the entrance of the MS stage;

the MS stage selectively operates in one of a total ion monitoring (TIM) mode, a single ion monitoring (SIM) mode, or a continuous scan mode; and the MS stage includes an ion detector that is capable of detecting negative and positive ions.

14. The combination as defined in claim 8, further comprising a fast faraday detector (FFD) coupled to one of the IMS stage, the DMS stage, and the MS stage, wherein:

the FFD includes an electrometer assembled with smaller values of resistors in series to divide the capacitance by the number of resistors in series accompanied by careful shielding; and the resistors in the electrometer are shielded to stop leakage caused by surface contaminations.

15. The combination as defined in claim 8, wherein:

the IMS stage comprises an inlet gate that operates as an ion shutter and comprises an outlet gate operable as an ion shutter and also operable as a peak detector, the IMS stage being controllable independently of the DMS stage and the MS stage to selectably operate in a high sensitivity mode with outlet gate operating as the peak detector and to selectably operate in a high selectivity mode with the outlet gate operating as the ion shutter to only pass ions that arrive at the outlet gate at a selectable time after the inlet gate opens;

the operating characteristics of the DMS stage are controllable independently of the IMS stage and the MS stage; and the operating characteristics of the MS stage are controllable independently of the IMS stage and the DMS stage.

16. A combination ion mobility spectrometer (IMS), differential mobility spectrometer (DMS) and mass spectrometer (MS) operated in series in at least two stages, comprising:

a sample inlet port that receives a input sample to be analyzed;

an ion source to ionize the input sample to produce an ionized sample; an ion mobility spectrometer (IMS) stage having an IMS inlet that receives the ionized sample and having an IMS outlet, the IMS having an electrical field that is applied to the ionized sample to move the ionized sample toward the IMS outlet; a high-field asymmetric-waveform ion mobility spectrometer (FAIMS) operating as a differential mobility spectrometer (DMS) stage coupled in series with the IMS stage to receive the ionized sample from the IMS stage; and a mass spectrometer (MS) stage coupled in series with the DMS stage to receive the ionized sample after the ionized sample passes through the DMS stage; a roughing vacuum pump to evacuate a first stage of the MS stage to a first pressure below atmospheric pressure; a high vacuum pump to evacuate a second stage of the MS stage to a second pressure below the first pressure; a vacuum interface positioned between the DMS and MS, wherein the vacuum interface comprises: a capillary skimmer positioned at the exit of the DMS cell to receive filtered ions exiting the DMS and inject the filter ions into a first end of a capillary, the viscous flow established inside the capillary skimmer transporting the ions to a second end of the capillary; a first pressure reduction stage comprising a chamber at a second end of the capillary, the first pressure reduction stage evacuated by a small roughing pump to reduce the ambient pressure to a first lower pressure to cause the ions exiting the second end of the capillary to experience a supersonic expansion; and a second pressure reduction stage separated from the first pressure reduction stage by a skimmer orifice located proximate the second end of the capillary, capillary, wherein the IMS stage comprises an ion mobility drift cell having a first ion, gate and a second ion gate, and wherein the combination further comprises a system controller that controls the release, the acceleration, and the timing of packets of ions produced in the ion source by controlling the first ion, gate and the second ion, gate of the ion mobility drift cell, the system controller selectively operating the first ion, gate and the second ion, gate in a first mode of operation and a second mode of operation, wherein: in the first mode of operation: the system controller opens the first ion, gate for a selected duration at the beginning of each detection cycle to inject a packet of ions into the IMS stage for pre-separation; the system controller opens the second ion, gate throughout the detection cycle; and the IMS stage producing an IMS spectrum by measuring the ion current in a Faraday detector in the IMS stage while the second ion gate remains open; and in the second mode of operation: the system controller opens the first ion, gate for a selected duration at the beginning of each detection cycle to inject a packet of ions into the IMS stage; and the system controller pulses the second ion, gate open at a selected time after opening the first ion, gate to control the ion flow by allowing only ions in selected peaks or in a section of the mobility spectrum to be transferred to the DMS stage in accordance with the travel time of the preselected analyte to be detected by the Faraday detector.

17. A combination ion mobility spectrometer (IMS), differential mobility spectrometer (DMS) and mass spectrometer (MS) operated in series in at least two stages, comprising: a sample inlet port that receives a input sample to be analyzed; an ion source to ionize the input sample to produce an ionized sample; an ion mobility spectrometer (IMS) stage having an IMS inlet that receives the ionized sample and having an IMS outlet, the IMS having an electrical field that is applied to the ionized sample to move the ionized sample toward the IMS outlet; a differential mobility spectrometer (DMS) stage coupled in series with the IMS stage to receive the ionized sample from the IMS stage; a mass spectrometer (MS) stage coupled in series with the DMS stage to receive the ionized sample after the ionized sample passes through the DMS stage; a roughing vacuum pump to evacuate a first stage of the MS stage to a first pressure below atmospheric pressure; a high vacuum pump to evacuate a second stage of the MS stage to a second pressure below the first pressure, wherein: the high vacuum pump for the second stage of the MS comprises an ion pump and a getter pump, wherein the getter pump sustains a low enough pressure to restart the ion pump after long periods of inactivity during which little or no power is supplied to the system; and the roughing pump for the first vacuum stage provides sufficient vacuum and flow capacity to start the high vacuum pump and to clear the sample gas from the MS, the roughing pump further operating as a sampling pump wherein the IMS stage comprises an ion mobility drift cell having a first ion gate and a second ion gate, and wherein the combination further comprises a system controller that controls the release, the acceleration, and the timing of packets of ions produced in the ion source by controlling the first ion gate and the second ion gate of the ion mobility drift cell, the system controller selectively operating the first ion gate and the second ion gate in a first mode of operation and a second mode of operation, wherein: in the first mode of operation: the system controller opens the first ion gate for a selected duration at the beginning of each detection cycle to inject a packet of ions into the IMS stage for pre separation; the system controller opens the second ion gate throughout the detection cycle; and the IMS stage producing an IMS spectrum by measuring the ion current in a Faraday detector in the IMS stage while the second ion gate remains open; and in the second mode of operation: the system controller opens the first ion gate for a selected duration at the beginning of each detection cycle to inject a packet of ions into the IMS stage; and the system controller pulses the second ion gate open at a selected time after opening the first ion gate to control the ion flow by allowing only ions in selected peaks or in a section of the mobility spectrum to be transferred to the DMS stage in accordance with the travel time of the preselected analyte to be detected by the Faraday detector.

\* \* \* \* \*